US012721676B2

(12) United States Patent
Beeckler et al.

(10) Patent No.: US 12,721,676 B2
(45) Date of Patent: Sep. 1, 2026

(54) BASKET CATHETER WITH CLOVERLEAF STRUCTURE TO PREVENT BUCKLING AND RETENTION FEATURE FOR ELECTRODES

(71) Applicant: Biosense Webster (Israel) Ltd., Yokneam (IL)

(72) Inventors: Christopher Thomas Beeckler, Brea, CA (US); Athanassios Papaioannou, Irvine, CA (US); Joseph Thomas Keyes, Sierra Madre, CA (US); Kevin Mark Okarski, Monrovia, CA (US); Justin George Lichter, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 447 days.

(21) Appl. No.: 18/192,296

(22) Filed: Mar. 29, 2023

(65) Prior Publication Data

US 2023/0346464 A1 Nov. 2, 2023

Related U.S. Application Data

(60) Provisional application No. 63/336,023, filed on Apr. 28, 2022, provisional application No. 63/336,094, filed on Apr. 28, 2022.

(51) Int. Cl.
*A61B 18/14* (2006.01)
*A61B 18/00* (2006.01)

(52) U.S. Cl.
CPC .. *A61B 18/1492* (2013.01); *A61B 2018/0016* (2013.01); *A61B 2018/00267* (2013.01);
(Continued)

(58) Field of Classification Search
CPC ........ A61B 18/1492; A61B 2018/0016; A61B 2018/00357; A61B 2018/00613;
(Continued)

(56) References Cited

U.S. PATENT DOCUMENTS

| | | | |
|---|---|---|---|
| 3,952,747 | A | 4/1976 | Kimmell, Jr. |
| 4,699,147 | A | 10/1987 | Chilson et al. |

(Continued)

FOREIGN PATENT DOCUMENTS

| | | | |
|---|---|---|---|
| CN | 104703557 | A | 6/2015 |
| CN | 105761835 | A | 7/2016 |

(Continued)

OTHER PUBLICATIONS

Extended European Search Report dated Feb. 2, 2023, from Corresponding European Application No. 22194819.3, 8 pages.

(Continued)

*Primary Examiner* — Joanne M Rodden
*Assistant Examiner* — Abigail Bock

(57) ABSTRACT

A medical probe is presented including an expandable basket assembly coupled to a distal end of a tubular shaft. The basket assembly includes a cloverleaf cutout structure at its distal end and spines extending proximally from the cloverleaf structure and coupling to the tubular shaft. The cloverleaf structure includes a sinusoidal-like member extending from one spine to an adjacent spine in a direction around the longitudinal axis. The sinusoidal-like member meanders around a first, second and third virtual circle such that the first and third virtual circles are approximately the same distance from a longitudinal axis of the medical probe and approximately the same size and the second virtual circle is between the first and second virtual circles, closer to the longitudinal axis, and having approximately 90% of the first open area of the first and third virtual circles.

20 Claims, 11 Drawing Sheets

(52) U.S. Cl.
CPC ............... *A61B 2018/00357* (2013.01); *A61B 2018/00577* (2013.01); *A61B 2018/00613* (2013.01); *A61B 2018/00767* (2013.01); *A61B 2018/1405* (2013.01); *A61B 2018/1467* (2013.01)

(58) Field of Classification Search
CPC .. A61B 2018/00767; A61B 2018/1405; A61B 2018/1467
See application file for complete search history.

(56) References Cited

U.S. PATENT DOCUMENTS 4,940,064 A 7/1990 Desai
5,215,103 A 6/1993 Desai
5,255,679 A 10/1993 Imran
5,293,869 A 3/1994 Edwards et al.
5,309,910 A 5/1994 Edwards et al.
5,313,943 A 5/1994 Houser et al.
5,324,284 A 6/1994 Imran
5,345,936 A 9/1994 Pomeranz et al.
5,365,926 A 11/1994 Desai
5,391,199 A 2/1995 Ben-Haim
5,396,887 A 3/1995 Imran
5,400,783 A 3/1995 Pomeranz et al.
5,411,025 A 5/1995 Webster, Jr.
5,415,166 A 5/1995 Imran
5,443,489 A 8/1995 Ben-Haim
5,456,254 A 10/1995 Pietroski et al.
5,465,717 A 11/1995 Imran et al.
5,476,495 A 12/1995 Kordis et al.
5,499,981 A 3/1996 Kordis
5,526,810 A 6/1996 Wang
5,546,940 A 8/1996 Panescu et al.
5,549,108 A 8/1996 Edwards et al.
5,558,073 A 9/1996 Pomeranz et al.
5,558,091 A 9/1996 Acker et al.
5,577,509 A 11/1996 Panescu et al.
5,595,183 A 1/1997 Swanson et al.
5,598,848 A 2/1997 Swanson et al.
5,609,157 A 3/1997 Panescu et al.
5,628,313 A 5/1997 Webster, Jr.
5,681,280 A 10/1997 Rusk et al.
5,718,241 A 2/1998 Ben-Haim et al.
5,722,401 A 3/1998 Pietroski et al.
5,722,403 A 3/1998 McGee et al.
5,725,525 A 3/1998 Kordis
5,730,128 A 3/1998 Pomeranz et al.
5,772,590 A 6/1998 Webster, Jr.
5,782,239 A 7/1998 Webster, Jr.
5,782,899 A 7/1998 Imran
5,823,189 A 10/1998 Kordis
5,881,727 A 3/1999 Edwards
5,893,847 A 4/1999 Kordis
5,904,680 A 5/1999 Kordis et al.
5,911,739 A 6/1999 Kordis et al.
5,928,228 A 7/1999 Kordis et al.
5,944,022 A 8/1999 Nardella et al.
5,968,040 A 10/1999 Swanson et al.
5,983,126 A 11/1999 Wittkampf
6,014,579 A 1/2000 Pomeranz et al.
6,014,590 A 1/2000 Whayne et al.
6,023,638 A 2/2000 Swanson
6,119,030 A 9/2000 Morency
6,142,993 A 11/2000 Whayne et al.
6,172,499 B1 1/2001 Ashe
6,198,974 B1 3/2001 Webster, Jr.
6,216,043 B1 4/2001 Swanson et al.
6,216,044 B1 4/2001 Kordis
6,239,724 B1 5/2001 Doron et al.
6,332,089 B1 12/2001 Acker et al.
6,428,537 B1 8/2002 Swanson et al.
6,456,864 B1 9/2002 Swanson et al.
6,484,118 B1 11/2002 Govari
6,574,492 B1 6/2003 Ben-Haim et al.
6,584,345 B2 6/2003 Govari
6,600,948 B2 7/2003 Ben-Haim et al.
6,618,612 B1 9/2003 Acker et al.
6,690,963 B2 2/2004 Ben-Haim et al.
6,738,655 B1 5/2004 Sen et al.
6,741,878 B2 5/2004 Fuimaono et al.
6,748,255 B2 6/2004 Fuimaono et al.
6,780,183 B2 8/2004 Jimenez, Jr. et al.
6,788,967 B2 9/2004 Ben-Haim et al.
6,837,886 B2 1/2005 Collins et al.
6,866,662 B2 3/2005 Fuimaono et al.
6,892,091 B1 5/2005 Ben-Haim et al.
6,970,730 B2 11/2005 Fuimaono et al.
6,973,340 B2 12/2005 Fuimaono et al.
6,980,858 B2 12/2005 Fuimaono et al.
6,987,995 B2 1/2006 Drysen
7,048,734 B1 5/2006 Fleischman et al.
7,142,903 B2 11/2006 Rodriguez et al.
7,149,563 B2 12/2006 Fuimaono et al.
7,255,695 B2 8/2007 Falwell et al.
7,257,434 B2 8/2007 Fuimaono et al.
7,274,957 B2 9/2007 Drysen
7,377,906 B2 5/2008 Selkee
7,399,299 B2 7/2008 Daniel et al.
7,410,486 B2 8/2008 Fuimaono et al.
7,522,950 B2 4/2009 Fuimaono et al.
7,536,218 B2 5/2009 Govari et al.
7,591,799 B2 9/2009 Selkee
7,593,760 B2 9/2009 Rodriguez et al.
RE41,334 E 5/2010 Beatty et al.
7,720,517 B2 5/2010 Drysen
7,756,576 B2 7/2010 Levin
7,794,473 B2 9/2010 Tessmer et al.
7,846,157 B2 12/2010 Kozel
7,848,787 B2 12/2010 Osadchy
7,853,302 B2 12/2010 Rodriguez et al.
7,869,865 B2 1/2011 Govari et al.
7,930,018 B2 4/2011 Harlev et al.
8,000,765 B2 8/2011 Rodriguez et al.
8,007,495 B2 8/2011 McDaniel et al.
8,021,327 B2 9/2011 Selkee
8,048,063 B2 11/2011 Aeby et al.
8,103,327 B2 1/2012 Harlev et al.
8,167,845 B2 5/2012 Wang et al.
8,224,416 B2 7/2012 De La Rama et al.
8,235,988 B2 8/2012 Davis et al.
8,275,440 B2 9/2012 Rodriguez et al.
8,295,902 B2 10/2012 Salahieh et al.
8,346,339 B2 1/2013 Kordis et al.
8,357,152 B2 1/2013 Govari et al.
8,435,232 B2 5/2013 Aeby et al.
8,447,377 B2 5/2013 Harlev et al.
8,456,182 B2 6/2013 Bar-Tal et al.
8,475,450 B2 7/2013 Govari et al.
8,498,686 B2 7/2013 Grunewald
8,517,999 B2 8/2013 Pappone et al.
8,545,490 B2 10/2013 Mihajlovic et al.
8,560,086 B2 10/2013 Just et al.
8,567,265 B2 10/2013 Aeby et al.
8,712,550 B2 4/2014 Grunewald
8,728,065 B2 5/2014 Fish et al.
8,755,861 B2 6/2014 Harlev et al.
8,825,130 B2 9/2014 Just et al.
8,906,011 B2 12/2014 Gelbart et al.
8,945,120 B2 2/2015 McDaniel et al.
8,979,839 B2 3/2015 De La Rama et al.
9,037,264 B2 5/2015 Just et al.
9,131,980 B2 9/2015 Bloom
9,204,929 B2 12/2015 Solis
9,277,960 B2 3/2016 Weinkam et al.
9,314,208 B1 4/2016 Altmann et al.
9,339,331 B2 5/2016 Tegg et al.
9,486,282 B2 11/2016 Solis
9,554,718 B2 1/2017 Bar-Tal et al.
9,566,111 B2 2/2017 Brannan et al.
D782,686 S 3/2017 Werneth et al.
9,585,588 B2 3/2017 Marecki et al.
9,597,036 B2 3/2017 Aeby et al.
9,687,297 B2 6/2017 Just et al.

(56) References Cited

U.S. PATENT DOCUMENTS 9,693,733 B2 7/2017 Altmann et al.
9,782,099 B2 10/2017 Williams et al.
9,788,895 B2 10/2017 Solis
9,801,681 B2 10/2017 Laske et al.
9,814,618 B2 11/2017 Nguyen et al.
9,833,161 B2 12/2017 Govari
9,848,795 B2 12/2017 Marecki et al.
9,894,756 B2 2/2018 Weinkam et al.
9,895,073 B2 2/2018 Solis
9,907,609 B2 3/2018 Cao et al.
9,974,460 B2 5/2018 Wu et al.
9,986,949 B2 6/2018 Govari et al.
9,993,160 B2 6/2018 Salvestro et al.
10,014,607 B1 7/2018 Govari et al.
10,028,376 B2 7/2018 Weinkam et al.
10,034,637 B2 7/2018 Harlev et al.
10,039,494 B2 8/2018 Altmann et al.
10,045,707 B2 8/2018 Govari
10,078,713 B2 9/2018 Auerbach et al.
10,111,623 B2 10/2018 Jung et al.
10,130,420 B2 11/2018 Basu et al.
10,136,828 B2 11/2018 Houben et al.
10,143,394 B2 12/2018 Solis
10,172,536 B2 1/2019 Maskara et al.
10,182,762 B2 1/2019 Just et al.
10,194,818 B2 2/2019 Williams et al.
10,201,311 B2 2/2019 Chou et al.
10,219,860 B2 3/2019 Harlev et al.
10,219,861 B2 3/2019 Just et al.
10,231,328 B2 3/2019 Weinkam et al.
10,238,309 B2 3/2019 Bar-Tal et al.
10,278,590 B2 5/2019 Salvestro et al.
D851,774 S 6/2019 Werneth et al.
10,314,505 B2 6/2019 Williams et al.
10,314,507 B2 6/2019 Govari et al.
10,314,648 B2 6/2019 Ge et al.
10,314,649 B2 6/2019 Bakos et al.
10,342,608 B2 7/2019 Wang et al.
10,349,855 B2 7/2019 Zeidan et al.
10,350,003 B2 7/2019 Weinkam et al.
10,362,991 B2 7/2019 Tran et al.
10,375,827 B2 8/2019 Weinkam et al.
10,376,170 B2 8/2019 Quinn et al.
10,376,221 B2 8/2019 Iyun et al.
10,398,348 B2 9/2019 Osadchy et al.
10,403,053 B2 9/2019 Katz et al.
10,441,188 B2 10/2019 Katz et al.
10,470,682 B2 11/2019 Deno et al.
10,470,714 B2 11/2019 Altmann et al.
10,482,198 B2 11/2019 Auerbach et al.
10,492,857 B2 12/2019 Guggenberger et al.
10,542,620 B2 1/2020 Weinkam et al.
10,575,743 B2 3/2020 Basu et al.
10,575,745 B2 3/2020 Solis
10,582,871 B2 3/2020 Williams et al.
10,582,894 B2 3/2020 Ben Zrihem et al.
10,596,346 B2 3/2020 Aeby et al.
10,602,947 B2 3/2020 Govari et al.
10,617,467 B2 4/2020 Viswanathan et al.
10,617,867 B2 4/2020 Viswanathan et al.
10,660,702 B2 5/2020 Viswanathan et al.
10,667,753 B2 6/2020 Werneth et al.
10,674,929 B2 6/2020 Houben et al.
10,681,805 B2 6/2020 Weinkam et al.
10,682,181 B2 6/2020 Cohen et al.
10,687,892 B2 6/2020 Long et al.
10,688,278 B2 6/2020 Beeckler et al.
10,702,178 B2 7/2020 Dahlen et al.
10,716,477 B2 7/2020 Salvestro et al.
10,758,304 B2 9/2020 Aujla
10,765,371 B2 9/2020 Hayam et al.
10,772,566 B2 9/2020 Aujila
10,799,281 B2 10/2020 Goertzen et al.
10,842,558 B2 11/2020 Harlev et al.
10,842,561 B2 11/2020 Viswanathan et al.
10,863,914 B2 12/2020 Govari et al.
10,881,376 B2 1/2021 Shemesh et al.
10,898,139 B2 1/2021 Guta et al.
10,905,329 B2 2/2021 Bar-Tal et al.
10,912,484 B2 2/2021 Ziv-Ari et al.
10,918,306 B2 2/2021 Govari et al.
10,939,871 B2 3/2021 Altmann et al.
10,952,795 B2 3/2021 Cohen et al.
10,973,426 B2 4/2021 Williams et al.
10,973,461 B2 4/2021 Baram et al.
10,987,045 B2 4/2021 Basu et al.
11,006,902 B1 5/2021 Bonyak et al.
11,040,208 B1 6/2021 Govari et al.
11,045,628 B2 6/2021 Beeckler et al.
11,051,877 B2 7/2021 Sliwa et al.
11,071,585 B2 7/2021 Zhang et al.
11,109,788 B2 9/2021 Rottmann et al.
11,116,435 B2 9/2021 Urman et al.
11,129,574 B2 9/2021 Cohen et al.
11,160,482 B2 11/2021 Solis
11,164,371 B2 11/2021 Yellin et al.
2002/0198522 A1 12/2002 Kordis et al.
2004/0210121 A1 10/2004 Fuimaono et al.
2006/0009689 A1 1/2006 Fuimaono et al.
2006/0009690 A1 1/2006 Fuimaono et al.
2006/0058813 A1 3/2006 Teague et al.
2006/0100669 A1 5/2006 Fuimaono et al.
2007/0093806 A1 4/2007 Desai et al.
2007/0276212 A1 11/2007 Fuimaono et al.
2008/0234564 A1 9/2008 Beatty et al.
2009/0149848 A1 6/2009 Werneth et al.
2010/0063478 A1 3/2010 Selkee
2011/0118726 A1 5/2011 De La Rama et al.
2011/0160574 A1 6/2011 Harlev et al.
2011/0190625 A1 8/2011 Harlev et al.
2011/0245756 A1 10/2011 Arora et al.
2011/0301597 A1 12/2011 Mcdaniel et al.
2012/0271136 A1 10/2012 Kordis et al.
2012/0271138 A1 10/2012 Kordis et al.
2012/0271140 A1 10/2012 Kordis et al.
2013/0090651 A1 4/2013 Smith
2013/0150693 A1 6/2013 D'Angelo
2013/0172715 A1 7/2013 Just et al.
2013/0172872 A1 7/2013 Subramaniam et al.
2013/0172883 A1 7/2013 Lopes et al.
2013/0178850 A1 7/2013 Lopes et al.
2013/0190587 A1 7/2013 Lopes et al.
2013/0296852 A1 11/2013 Madjarov et al.
2014/0025069 A1 1/2014 Willard et al.
2014/0052118 A1 2/2014 Laske et al.
2014/0088588 A1 3/2014 Jarrard
2014/0180147 A1 6/2014 Thakur et al.
2014/0180151 A1 6/2014 Maskara et al.
2014/0180152 A1 6/2014 Maskara et al.
2014/0200578 A1 7/2014 Groff et al.
2014/0257069 A1 9/2014 Eliason et al.
2014/0276712 A1 9/2014 Mallin et al.
2014/0276746 A1 9/2014 Nabutovsky et al.
2014/0288552 A1* 9/2014 Kunis ................ A61B 18/1815
606/41
2014/0309512 A1 10/2014 Govari et al.
2014/0309513 A1 10/2014 Fish et al.
2014/0350551 A1 11/2014 Raatikka et al.
2015/0011991 A1 1/2015 Buysman et al.
2015/0045863 A1 2/2015 Litscher et al.
2015/0080693 A1 3/2015 Solis
2015/0105770 A1 4/2015 Amit
2015/0119878 A1 4/2015 Heisel et al.
2015/0133919 A1 5/2015 Mcdaniel et al.
2015/0208942 A1 7/2015 Bar-Tal et al.
2015/0223757 A1 8/2015 Werneth et al.
2015/0250424 A1 9/2015 Govari et al.
2015/0270634 A1 9/2015 Buesseler et al.
2015/0282859 A1 10/2015 Bencini et al.
2015/0342491 A1 12/2015 Marecki et al.
2015/0342532 A1 12/2015 Basu et al.
2015/0351625 A1 12/2015 Schroth et al.
2015/0366508 A1 12/2015 Chou et al.
2016/0081746 A1 3/2016 Solis

(56) References Cited

U.S. PATENT DOCUMENTS

2016/0113582 A1 4/2016 Altmann et al.
2016/0113709 A1 4/2016 Maor
2016/0183877 A1 6/2016 Williams et al.
2016/0228023 A1 8/2016 Govari
2016/0228062 A1 8/2016 Altmann et al.
2016/0278853 A1 9/2016 Ogle et al.
2016/0302858 A1 10/2016 Bencini
2016/0324573 A1 11/2016 Mickelson et al.
2016/0338770 A1 11/2016 Bar-Tal et al.
2017/0027638 A1 2/2017 Solis
2017/0035496 A1 2/2017 Nagale et al.
2017/0035497 A1 2/2017 Nagale et al.
2017/0065227 A1 3/2017 Marrs et al.
2017/0071543 A1 3/2017 Basu et al.
2017/0071544 A1 3/2017 Basu et al.
2017/0071665 A1 3/2017 Solis
2017/0095173 A1 4/2017 Bar-Tal et al.
2017/0100187 A1 4/2017 Basu et al.
2017/0143227 A1 5/2017 Marecki et al.
2017/0156790 A1 6/2017 Aujla
2017/0164858 A1 6/2017 Basu
2017/0172442 A1 6/2017 Govari
2017/0172651 A1 6/2017 Gross et al.
2017/0185702 A1 6/2017 Auerbach et al.
2017/0202515 A1 7/2017 Zrihem et al.
2017/0221262 A1 8/2017 Laughner et al.
2017/0224958 A1 8/2017 Cummings et al.
2017/0265812 A1 9/2017 Williams et al.
2017/0281031 A1 10/2017 Houben et al.
2017/0281268 A1 10/2017 Tran et al.
2017/0296125 A1 10/2017 Altmann et al.
2017/0296251 A1 10/2017 Wu et al.
2017/0319140 A1* 11/2017 Wu ..................... A61B 5/6859
2017/0347959 A1 12/2017 Guta et al.
2017/0354338 A1 12/2017 Levin et al.
2017/0354339 A1 12/2017 Zeidan et al.
2017/0354364 A1 12/2017 Bar-Tal et al.
2018/0000540 A1 1/2018 Ogle et al.
2018/0008203 A1 1/2018 Iyun et al.
2018/0028084 A1 2/2018 Williams et al.
2018/0049803 A1 2/2018 Solis
2018/0085064 A1 3/2018 Auerbach et al.
2018/0116595 A1 5/2018 Ruppersberg
2018/0132749 A1 5/2018 Govari et al.
2018/0137687 A1 5/2018 Katz et al.
2018/0160936 A1 6/2018 Govari et al.
2018/0160978 A1 6/2018 Cohen et al.
2018/0168511 A1 6/2018 Hall et al.
2018/0184982 A1 7/2018 Basu et al.
2018/0192958 A1 7/2018 Wu
2018/0192959 A1 7/2018 Mou et al.
2018/0206792 A1 7/2018 Auerbach et al.
2018/0228439 A1 8/2018 Wu et al.
2018/0235692 A1 8/2018 Efimov et al.
2018/0249959 A1 9/2018 Osypka
2018/0256109 A1 9/2018 Wu et al.
2018/0279954 A1 10/2018 Hayam et al.
2018/0303414 A1 10/2018 Toth et al.
2018/0303546 A1 10/2018 Buysman et al.
2018/0310987 A1 11/2018 Altmann et al.
2018/0311497 A1 11/2018 Viswanathan et al.
2018/0338722 A1 11/2018 Altmann et al.
2018/0344188 A1 12/2018 Govari
2018/0344202 A1 12/2018 Bar-Tal et al.
2018/0344251 A1 12/2018 Harlev et al.
2018/0344393 A1 12/2018 Gruba et al.
2018/0360534 A1 12/2018 Teplitsky et al.
2018/0365355 A1 12/2018 Auerbach et al.
2019/0000540 A1 1/2019 Cohen et al.
2019/0008582 A1 1/2019 Govari et al.
2019/0015007 A1 1/2019 Rottmann et al.
2019/0030328 A1 1/2019 Stewart et al.
2019/0053708 A1 2/2019 Gliner
2019/0059766 A1 2/2019 Houben et al.
2019/0069950 A1 3/2019 Viswanathan et al.
2019/0069954 A1 3/2019 Cohen et al.
2019/0117111 A1 4/2019 Osadchy et al.
2019/0117303 A1 4/2019 Claude et al.
2019/0117315 A1 4/2019 Keyes et al.
2019/0125338 A1 5/2019 Shelton, IV et al.
2019/0125437 A1 5/2019 Govari et al.
2019/0125439 A1 5/2019 Rohl et al.
2019/0133552 A1 5/2019 Shemesh et al.
2019/0142293 A1 5/2019 Solis
2019/0164633 A1 5/2019 Ingel et al.
2019/0167137 A1 6/2019 Bar-Tal et al.
2019/0167140 A1 6/2019 Williams et al.
2019/0188909 A1 6/2019 Yellin et al.
2019/0201664 A1 7/2019 Govari
2019/0209089 A1 7/2019 Baram et al.
2019/0216346 A1 7/2019 Ghodrati et al.
2019/0216347 A1 7/2019 Ghodrati et al.
2019/0231421 A1 8/2019 Viswanathan et al.
2019/0231423 A1 8/2019 Weinkam et al.
2019/0239811 A1 8/2019 Just et al.
2019/0246935 A1 8/2019 Govari et al.
2019/0298442 A1 10/2019 Ogata et al.
2019/0314083 A1 10/2019 Herrera et al.
2019/0328260 A1 10/2019 Zeidan et al.
2019/0336210 A1 11/2019 Beeckler et al.
2019/0343580 A1 11/2019 Nguyen et al.
2019/0350567 A1 11/2019 Cummins et al.
2019/0350647 A1 11/2019 Ramberg et al.
2020/0000518 A1 1/2020 Kiernan et al.
2020/0008705 A1 1/2020 Ziv-Ari et al.
2020/0008869 A1 1/2020 Byrd
2020/0009378 A1 1/2020 Stewart et al.
2020/0015876 A1 1/2020 Chou et al.
2020/0015890 A1 1/2020 To et al.
2020/0022653 A1 1/2020 Moisa
2020/0029845 A1 1/2020 Baram et al.
2020/0046421 A1 2/2020 Govari
2020/0046423 A1 2/2020 Viswanathan et al.
2020/0060569 A1 2/2020 Tegg
2020/0077959 A1 3/2020 Altmann et al.
2020/0093539 A1 3/2020 Long et al.
2020/0129089 A1 4/2020 Gliner et al.
2020/0129125 A1 4/2020 Govari et al.
2020/0129128 A1 4/2020 Gliner et al.
2020/0163707 A1 5/2020 Sliwa et al.
2020/0179650 A1 6/2020 Beeckler et al.
2020/0196896 A1 6/2020 Solis
2020/0197082 A1 6/2020 Daniel et al.
2020/0205689 A1 7/2020 Squires et al.
2020/0205690 A1 7/2020 Williams et al.
2020/0205737 A1 7/2020 Beeckler
2020/0205876 A1 7/2020 Govari
2020/0205890 A1 7/2020 Harlev et al.
2020/0205892 A1 7/2020 Viswanathan et al.
2020/0206461 A1 7/2020 Govari et al.
2020/0206498 A1 7/2020 Arora et al.
2020/0289197 A1 9/2020 Viswanathan et al.
2020/0297234 A1 9/2020 Houben et al.
2020/0297281 A1 9/2020 Basu et al.
2020/0305726 A1 10/2020 Salvestro et al.
2020/0305946 A1 10/2020 Desimone et al.
2020/0375657 A1 12/2020 Olson et al.
2020/0397328 A1 12/2020 Altmann et al.
2020/0398048 A1 12/2020 Krimsky et al.
2021/0015549 A1 1/2021 Haghighi-Mood et al.
2021/0022684 A1 1/2021 Govari et al.
2021/0045805 A1 2/2021 Govari et al.
2021/0059549 A1 3/2021 Urman et al.
2021/0059550 A1 3/2021 Urman et al.
2021/0059608 A1 3/2021 Beeckler et al.
2021/0059743 A1 3/2021 Govari
2021/0059747 A1 3/2021 Krans et al.
2021/0077180 A1 3/2021 Govari et al.
2021/0077184 A1 3/2021 Basu et al.
2021/0082157 A1 3/2021 Rosenberg et al.
2021/0085200 A1 3/2021 Auerbach et al.
2021/0085204 A1 3/2021 Auerbach et al.
2021/0085215 A1 3/2021 Auerbach et al.
2021/0085387 A1 3/2021 Amit et al.

(56) References Cited

U.S. PATENT DOCUMENTS

2021/0093292 A1 4/2021 Baram et al.
2021/0093294 A1 4/2021 Shemesh et al.
2021/0093374 A1 4/2021 Govari et al.
2021/0093376 A1 4/2021 Harlev et al.
2021/0093377 A1 4/2021 Herrera et al.
2021/0100612 A1 4/2021 Baron et al.
2021/0113822 A1 4/2021 Beeckler et al.
2021/0127999 A1 5/2021 Govari et al.
2021/0128010 A1 5/2021 Govari et al.
2021/0133516 A1 5/2021 Govari et al.
2021/0145282 A1 5/2021 Bar-Tal et al.
2021/0161582 A1 6/2021 Byrd et al.
2021/0161592 A1 6/2021 Altmann et al.
2021/0162210 A1 6/2021 Altmann et al.
2021/0169421 A1 6/2021 Govari
2021/0169550 A1 6/2021 Govari et al.
2021/0169567 A1 6/2021 Govari et al.
2021/0169568 A1 6/2021 Govari et al.
2021/0177294 A1 6/2021 Gliner et al.
2021/0177356 A1 6/2021 Gliner et al.
2021/0177503 A1 6/2021 Altmann et al.
2021/0178166 A1 6/2021 Govari et al.
2021/0186363 A1 6/2021 Gliner et al.
2021/0186604 A1 6/2021 Altmann et al.
2021/0187241 A1 6/2021 Govari et al.
2021/0187254 A1 6/2021 Beeckler et al.
2021/0196372 A1 7/2021 Altmann et al.
2021/0196394 A1 7/2021 Govari et al.
2021/0212591 A1 7/2021 Govari et al.
2021/0219904 A1 7/2021 Yarnitsky et al.
2021/0236815 A1 8/2021 Waldstreicher et al.
2021/0267672 A1 9/2021 Tegg et al.
2021/0278936 A1 9/2021 Katz et al.
2021/0282659 A1 9/2021 Govari et al.
2021/0307815 A1* 10/2021 Govari ............... A61B 18/1206
2021/0308424 A1 10/2021 Beeckler et al.
2021/0338319 A1 11/2021 Govari et al.
2021/0369339 A1 12/2021 Salazar et al.
2022/0071694 A1 3/2022 Govari et al.
2022/0071695 A1 3/2022 Beeckler et al.
2022/0071696 A1 3/2022 Beeckler et al.
2022/0087736 A1 3/2022 Govari et al.
2022/0110679 A1 4/2022 Wang et al.
2022/0304745 A1 9/2022 Olson
2022/0387051 A1 12/2022 Girdhar
2023/0000550 A1 1/2023 Nedved et al.
2023/0130692 A1 4/2023 Wang et al.
2023/0225790 A1 7/2023 Okarski
2023/0346455 A1 11/2023 Beeckler et al.
2023/0346459 A1 11/2023 Beeckler et al.
2023/0346462 A1 11/2023 Beeckler et al.
2023/0346464 A1 11/2023 Beeckler et al.
2023/0346466 A1* 11/2023 Keyes .................... A61B 5/333
2024/0216045 A1 7/2024 Keyes
2025/0057589 A1 2/2025 Sandquist et al.

FOREIGN PATENT DOCUMENTS

CN 106510683 A 3/2017
CN 107343816 A 11/2017
CN 108272505 A 7/2018
CN 110461262 A 11/2019
CN 111248993 A 6/2020
CN 111248996 A 6/2020
CN 111491582 A 8/2020
CN 113491572 A 10/2021
EP 0668740 A1 8/1995
EP 0644738 B1 3/2000
EP 0727183 B1 11/2002
EP 0727184 B1 12/2002
EP 2201905 A1 6/2010
EP 2783651 A1 10/2014
EP 2699151 B1 11/2015
EP 2699152 B1 11/2015
EP 2699153 B1 12/2015
EP 2498706 B1 4/2016
EP 2578173 B1 6/2017
EP 3181082 A1 6/2017
EP 3238645 A1 11/2017
EP 2884931 B1 1/2018
EP 3315086 A1 5/2018
EP 2349440 B1 8/2019
EP 3318211 B1 12/2019
EP 3581135 A1 12/2019
EP 2736434 B1 2/2020
EP 3451962 B1 3/2020
EP 3791816 A2 3/2021
EP 3972510 A1 3/2022
EP 4115834 A1 1/2023
WO WO-9421167 A1 9/1994
WO WO-9421169 A1 9/1994
WO WO-9625095 A1 8/1996
WO WO-9634560 A1 11/1996
WO WO-0182814 A2 11/2001
WO WO-2004087249 A2 10/2004
WO WO-2012100185 A2 7/2012
WO WO-2013052852 A1 4/2013
WO WO-2013162884 A1 10/2013
WO WO-2013173917 A1 11/2013
WO WO-2013176881 A1 11/2013
WO WO-2014176205 A1 10/2014
WO WO-2016019760 A1 2/2016
WO WO-2016044687 A1 3/2016
WO WO-2018111600 A1 6/2018
WO WO-2018191149 A1 10/2018
WO WO-2019084442 A1 5/2019
WO WO-2019143960 A1 7/2019
WO WO-2020026217 A1 2/2020
WO 2020194216 A1 10/2020
WO WO-2020206328 A1 10/2020
WO 2021181231 A2 9/2021
WO 2021250538 A1 12/2021
WO 2022001908 A1 1/2022

OTHER PUBLICATIONS

Extended European Search Report and Opinion dated Jun. 1, 2023, from corresponding European Application No. 23152493.5.
Extended European Search Report and Opinion dated Jun. 7, 2023, from corresponding European Application No. 23152399.4.
Extended European Search Report and Opinion dated Jun. 12, 2023, from corresponding European Application No. 23152448.9.
Extended European Search Report dated Jun. 13, 2023, from Corresponding European Application No. 23152458.8, 12 pages.
Extended European Search Report and Opinion dated Sep. 6, 2023, from corresponding European Application No. 23152472.9.
Extended European Search Report & Search Opinion dated Sep. 19, 2023, from corresponding European Application No. 23170233.3.
Extended European Search Report & Search Opinion dated Sep. 19, 2023, from corresponding European Application No. 23170325.7.
Extended European Search Report & Search Opinion dated Sep. 21, 2023, from corresponding European Application No. 23170230.9.
Extended European Search Report & Search Opinion dated Sep. 21, 2023, from corresponding European Application No. 23170409.9.
Extended European Search Report & Search Opinion dated Jan. 2, 2024, from corresponding European Application No. 23170297.8.
Extended European Search Report and Opinion dated Jun. 15, 2023, from corresponding European Application No. 23152482.8.
Extended European Search Report and Opinion dated Sep. 19, 2023, from corresponding European Application No. 23170233.3.
Extended European Search Report and Opinion dated Sep. 21, 2023, from corresponding European Application No. 23170409.9.
First Search dated Dec. 3, 2025, from corresponding Chinese Application No. 202210980943.X.
First Office Action with English translation dated Dec. 3, 2025, from corresponding Chinese Application No. 202210980943.X.
Novelty Search Report dated Jan. 22, 2024, from corresponding Chinese Application No. 202410010913.5.

* cited by examiner

BASKET CATHETER WITH CLOVERLEAF STRUCTURE TO PREVENT BUCKLING AND RETENTION FEATURE FOR ELECTRODES

CROSS-REFERENCE TO RELATED APPLICATIONS

This application claims priority under 35 U.S.C. § 119 to prior filed U.S. Provisional Patent Application No. 63/336,023 filed Apr. 28, 2022 and U.S. Provisional Patent Application No. 63/336,094 filed Apr. 28, 2022, each of which are hereby incorporated by reference as if set forth in full herein.

FIELD

The present invention relates generally to medical devices, and in particular catheters with substantially ovoid or trapezoidal electrodes, and further relates to, but not exclusively, catheters suitable for use to induce irreversible electroporation (IRE) of cardiac tissues.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Many current ablation approaches in the art tend to utilize radiofrequency (RF) electrical energy to heat tissue. RF ablation can have certain rare drawbacks due to operator's skill, such as heightened risk of thermal cell injury which can lead to tissue charring, burning, steam pop, phrenic nerve palsy, pulmonary vein stenosis, and esophageal fistula. Cryoablation is an alternative approach to RF ablation that can reduce some thermal risks associated with RF ablation but may present tissue damage due to the very low temperature nature of such devices. Maneuvering cryoablation devices and selectively applying cryoablation, however, is generally more challenging compared to RF ablation; therefore, cryoablation is not viable in certain anatomical geometries which may be reached by electrical ablation devices.

Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of IRE energy to tissues using multi-electrode catheters was previously proposed in the patent literature. Examples of systems and devices configured for IRE ablation are disclosed in U.S. Patent Pub. No. 2021/0169550A1, 2021/0169567A1, 2021/0169568A1, 2021/0161592A1, 2021/0196372A1, 2021/0177503A1, and 2021/0186604A1, each of which are incorporated herein by reference and attached in the Appendix of priority U.S. Provisional Patent Application No. 63/336,023.

Regions of cardiac tissue can be mapped by a catheter to identify the abnormal electrical signals. The same or different catheter can be used to perform ablation. Some example catheters include a number of spines with electrodes positioned thereon. The electrodes are generally attached to the spines and secured in place by soldering, welding, or using an adhesive. Furthermore, multiple linear spines are generally assembled together by attaching both ends of the linear spines to a tubular shaft (e.g., a pusher tube) to form a spherical basket. Due to the small size of the spines and the electrodes, however, adhering the electrodes to the spines and then forming a spherical basket from the multiple linear spines can be a difficult task, increasing the manufacturing time and cost and the chances that the electrode fails due to an improper bond or misalignment. What is needed, therefore, are devices and methods of forming an improved basket assembly that can help to reduce the time required for manufacturing the basket assembly, alternative catheter geometries, and alternative electrode shapes and sizes in general.

DETAILED DESCRIPTION

Figure 1:
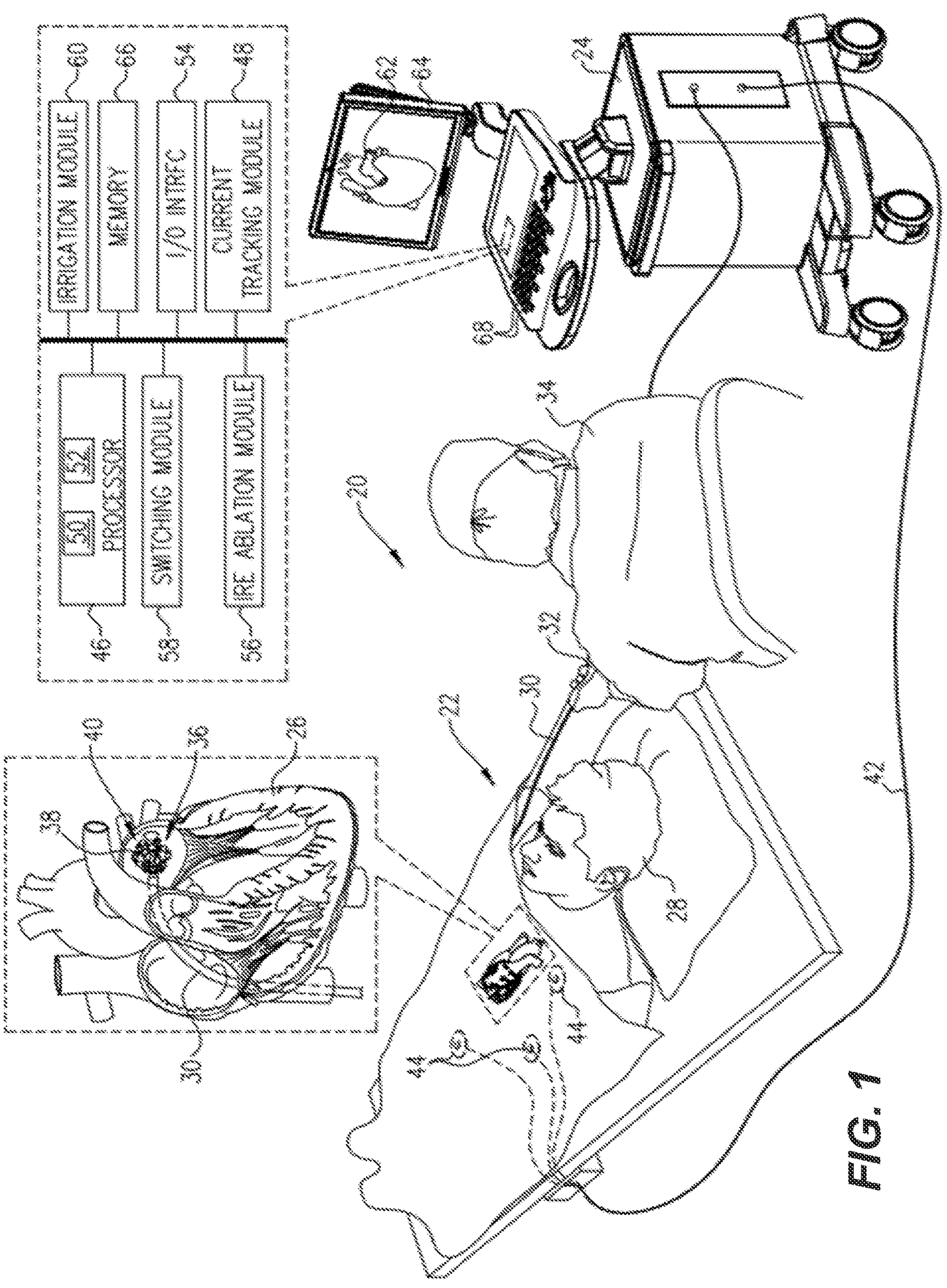
FIG. 1 is a schematic pictorial illustration of a medical system including a medical probe whose distal end includes a basket assembly with electrodes, in accordance with an embodiment of the present invention.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

As used herein, the terms "patient," "host," "user," and "subject" refer to any human or animal subject and are not intended to limit the systems or methods to human use, although use of the subject invention in a human patient represents a preferred embodiment. In addition, vasculature of a "patient," "host," "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example. As well, the term "proximal" indicates a location closer to the operator or physician whereas "distal" indicates a location further away to the operator or physician.

As discussed herein, "operator" can include a doctor, surgeon, technician, scientist, or any other individual or delivery instrumentation associated with delivery of a multi-electrode catheter for the treatment of drug refractory atrial fibrillation to a subject.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as irreversible electroporation (IRE), referred throughout this disclosure interchangeably as pulsed electric field (PEF) and pulsed field ablation (PFA). Ablating or ablation as it relates to the devices and corresponding systems of this disclosure is used throughout this disclosure in reference to non-thermal ablation of cardiac tissue for certain conditions including, but not limited to, arrhythmias, atrial fibrillation ablation, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "bipolar" and "unipolar" when used to refer to ablation schemes describe ablation schemes which differ with respect to electrical current path and electric field distribution. "Bipolar" refers to ablation scheme utilizing a current path between two or more electrodes that are both positioned at a treatment site; current density and electric flux density is typically approximately equal at each of the electrodes. "Unipolar" refers to ablation scheme utilizing a current path between two or more electrodes, wherein a first electrode or combination of electrodes experiences a high current density and high electric flux density and is positioned at a treatment site, and a second electrode or series of electrodes experiences comparatively lower current density and lower electric flux density and is positioned remotely from the treatment site.

As discussed herein, the terms "biphasic pulse" and "monophasic pulse" refer to respective electrical signals. "Biphasic pulse" refers to an electrical signal including a positive-voltage phase pulse (referred to herein as "positive phase") and a negative-voltage phase pulse (referred to herein as "negative phase"). "Monophasic pulse" refers to an electrical signal including only a positive or only a negative phase. Preferably, a system providing the biphasic pulse is configured to prevent application of a direct current voltage (DC) to a patient. For instance, the average voltage of the biphasic pulse can be zero volts with respect to ground or other common reference voltage. Additionally, or alternatively, the system can include a capacitor or other protective component. Where voltage amplitude of the biphasic and/or monophasic pulse is described herein, it is understood that the expressed voltage amplitude is an absolute value of the approximate peak amplitude of each of the positive-voltage phase and/or the negative-voltage phase. Each phase of the biphasic and monophasic pulse preferably has a square shape including an essentially constant voltage amplitude during a majority of the phase duration. Phases of the biphasic pulse are separated in time by an interphase delay. The interphase delay duration is preferably less than or approximately equal to the duration of a phase of the biphasic pulse. The interphase delay duration is more preferably about 25% of the duration of the phase of the biphasic pulse.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer surface without departing from the scope of the present disclosure.

The term "temperature rating", as used herein, is defined as the maximum continuous temperature that a component can withstand during its lifetime without causing thermal damage, such as melting or thermal degradation (e.g., charring and crumbling) of the component.

The present disclosure is related to systems, methods or uses and devices which utilize end effectors including electrodes affixed to spines. Example systems, methods, and devices of the present disclosure may be particularly suited for IRE ablation of cardiac tissue to treat cardiac arrhythmias. Ablative energies are typically provided to cardiac tissue by a tip portion of a catheter which can deliver ablative energy alongside the tissue to be ablated. Some example catheters include three-dimensional structures at the tip portion and are configured to administer ablative energy from various electrodes positioned on the three-dimensional structures. Ablative procedures incorporating such example catheters can be visualized using fluoroscopy, ultrasound, and/or a 3D mapping system utilizing magnetic and/or impedance based navigation.

Ablation of cardiac tissue using application of a thermal technique, such as radio frequency (RF) energy and cryoablation, to correct a malfunctioning heart is a well-known procedure. Typically, to successfully ablate using a thermal technique, cardiac electropotentials need to be measured at various locations of the myocardium. In addition, temperature measurements during ablation provide data enabling the efficacy of the ablation. Typically, for an ablation procedure using a thermal technique, the electropotentials and the temperatures are measured before, during, and after the actual ablation.

RF approaches can have risks that can lead to tissue charring, burning, steam pop, phrenic nerve palsy, pulmonary vein stenosis, and esophageal fistula. Cryoablation is an alternative approach to RF ablation that can reduce some thermal risks associated with RF ablation. However maneuvering cryoablation devices and selectively applying cryoablation is generally more challenging compared to RF ablation; therefore, cryoablation is not viable in certain anatomical geometries which may be reached by electrical ablation devices.

IRE as discussed in this disclosure is a non-thermal cell death technology that can be used for ablation of atrial arrhythmias. To ablate using IRE/PEF, biphasic voltage pulses are applied to disrupt cellular structures of the myocardium. The biphasic pulses are non-sinusoidal and can be tuned to target cells based on electrophysiology of the cells. In contrast, to ablate using RF, a sinusoidal voltage waveform is applied to produce heat at the treatment area, indiscriminately heating all cells in the treatment area. IRE therefore has the capability to spare adjacent heat sensitive structures or tissues which would be of benefit in the reduction of possible complications known with ablation or isolation modalities. Additionally, or alternatively, monophasic pulses can be utilized.

Electroporation can be induced by applying a pulsed electric field across biological cells to cause reversable (temporary) or irreversible (permanent) creation of pores in the cell membrane. The cells have a transmembrane electrostatic potential that is increased above a resting potential upon application of the pulsed electric field. While the transmembrane electrostatic potential remains below a threshold potential, the electroporation is reversable, meaning the pores can close when the applied pulse electric field is removed, and the cells can self-repair and survive. If the transmembrane electrostatic potential increases beyond the threshold potential, the electroporation is irreversible, and the cells become permanently permeable. As a result, the cells die due to a loss of homeostasis and typically die by programmed cell death or apoptosis, which is believed to leave less scar tissue as compared to other ablation modalities. Generally, cells of differing types have differing threshold potential. For instance, heart cells have a threshold potential of approximately 500 V/cm, whereas for bone it is 3000 V/cm. These differences in threshold potential allow IRE to selectively target tissue based on threshold potential.

The solution of this disclosure includes systems and methods for applying electrical signals from catheter electrodes positioned in the vicinity of myocardial tissue, preferably by applying a pulsed electric field effective to induce electroporation in the myocardial tissue. The systems and methods can be effective to ablate targeted tissue by inducing irreversible electroporation. In some examples, the systems and methods can be effective to induce reversible electroporation as part of a diagnostic procedure. Reversible electroporation occurs when the voltage applied with the electrodes is below the electric field threshold of the target tissue allowing cells to repair. Reversible electroporation does not kill the cells but allows a physician to see the effect of reversible electroporation on electrical activation signals in the vicinity of the target location. Example systems and methods for reversible electroporation is disclosed in U.S. Patent Publication 2021/0162210, the entirety of which is incorporated herein by reference and attached in the Appendix of priority U.S. Provisional Patent Application No. 63/336,023.

The pulsed electric field, and its effectiveness to induce reversible and/or irreversible electroporation, can be affected by physical parameters of the system and biphasic pulse parameters of the electrical signal. Physical parameters can include electrode contact area, electrode spacing, electrode geometry, etc. examples presented herein generally include physical parameters adapted to effectively induce reversible and/or irreversible electroporation. Biphasic pulse parameters of the electrical signal can include voltage amplitude, pulse duration, pulse interphase delay, inter-pulse delay, total application time, delivered energy, etc. In some examples, parameters of the electrical signal can be adjusted to induce both reversible and irreversible electroporation given the same physical parameters. Examples of various systems and methods of ablation including IRE are presented in U.S. Patent Publications 2021/0169550A1, 2021/0169567A1, 2021/0169568A1, 2021/0161592A1, 2021/0196372A1, 2021/0177503A1, and 2021/0186604A1, the entireties of each of which are incorporated herein by reference and attached in the Appendix of priority U.S. Provisional Patent Application No. 63/336,023.

To deliver pulsed field ablation (PFA) in an IRE (irreversible electroporation) procedure, electrodes should contact the tissue being ablated with a sufficiently large surface area. As described hereinbelow, the medical probe includes a tubular shaft including proximal and distal ends, and a basket assembly at the distal end of the tubular shaft. The basket assembly includes a single unitary structure. The unitary structure can include a plurality of linear spines formed from a planar sheet of material or tube stock and one or more electrodes coupled to each of the spines. The plurality of linear spines can converge at a central spine intersection including one or more cutouts. The cutouts can allow for bending of each spine such that the spines form an approximately spherical or oblate-spheroid basket assembly. Itis noted that the cutouts (in various configurations described and illustrated in the specification) allows the basket to be compressed into a much smaller form factor when undeployed (or undergoing a retraction into a delivery sheath) without buckling or plastic deformation.

FIG. 1 is a schematic, pictorial illustration of a medical system 20 including a medical probe 22 and a control console 24, in accordance with an embodiment of the present invention. Medical system 20 may be based, for example, on the CARTO® system, produced by Biosense Webster Inc. of 31 Technology Drive, Suite 200, Irvine, CA 92618 USA. In embodiments described hereinbelow, medical probe 22 can be used for diagnostic or therapeutic treatment, such as for performing ablation procedures in a heart 26 of a patient 28. Alternatively, medical probe 22 may be used, mutatis mutandis, for other therapeutic and/or diagnostic purposes in the heart or in other body organs.

Medical probe 22 includes a flexible insertion tube 30 and a handle 32 coupled to a proximal end of the tubular shaft. During a medical procedure, a medical professional 34 can insert probe 22 through the vascular system of patient 28 so that a distal end 39 of the medical probe enters a body cavity such as a chamber of heart 26. Upon distal end 39 entering the chamber of heart 26, medical professional 34 can deploy a basket assembly 38 approximate a distal end 39 of the medical probe 22. Basket assembly 38 can include a plurality of electrodes 40 affixed to a plurality of spines 214, as described in the description referencing FIGS. 2A, 2B, 2C, 3A, and 3B hereinbelow. To start performing a medical procedure such as irreversible electroporation (IRE) ablation, medical professional 34 can manipulate handle 32 to position distal end 39 so that electrodes 40 engage cardiac tissue at a desired location or locations. Upon positioning the distal end 39 so that electrodes 40 (disposed on an extension structure 38) engages cardiac tissue, the medical professional 34 can activate the medical probe 22 such that electrical pulses are delivered by the electrodes 40 to perform the IRE ablation.

Figure 2A:
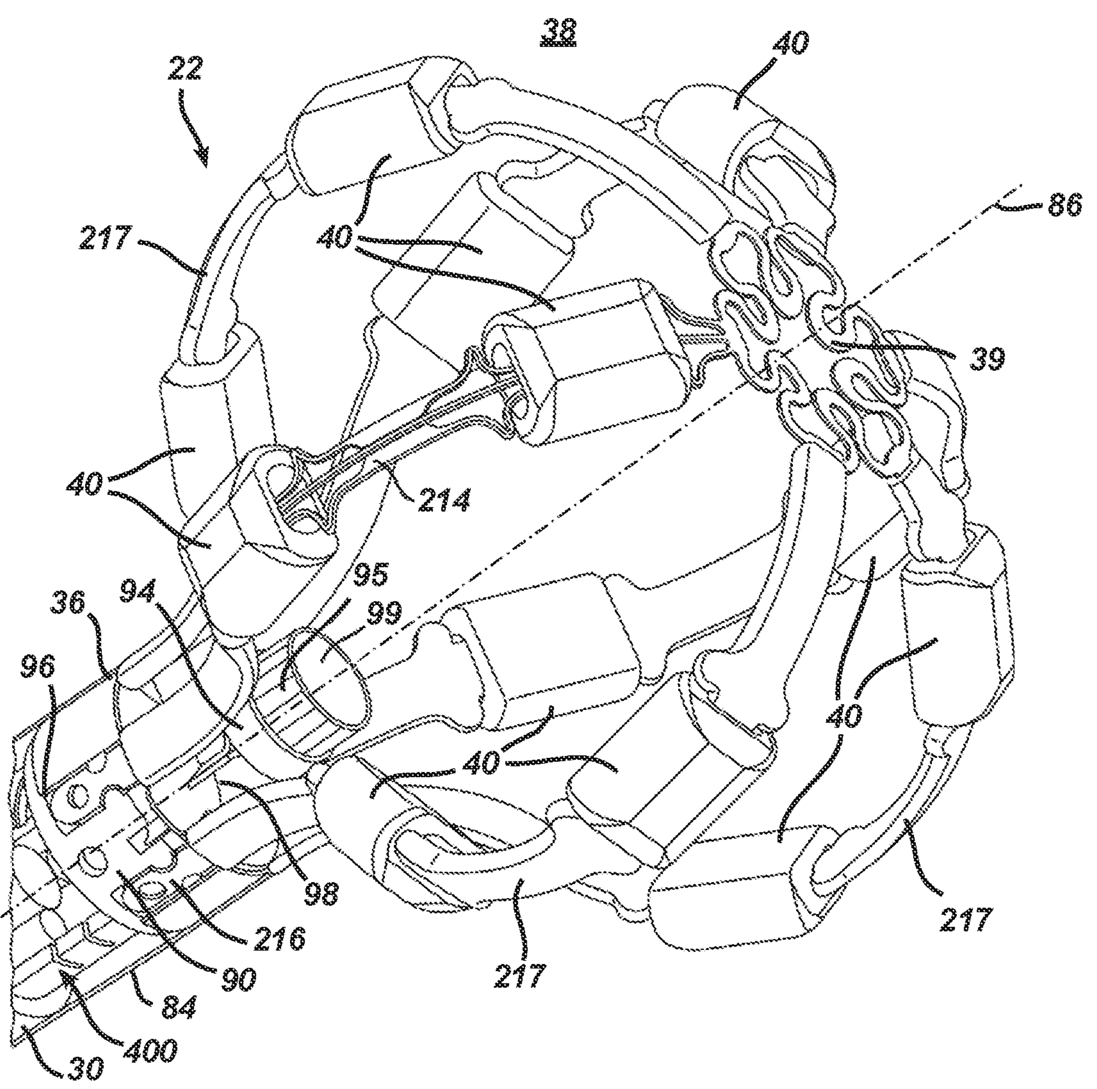
FIG. 2A is a perspective view of a medical probe in an expanded form, in accordance with a prototype or embodiment of the present invention.
Figure 2B:
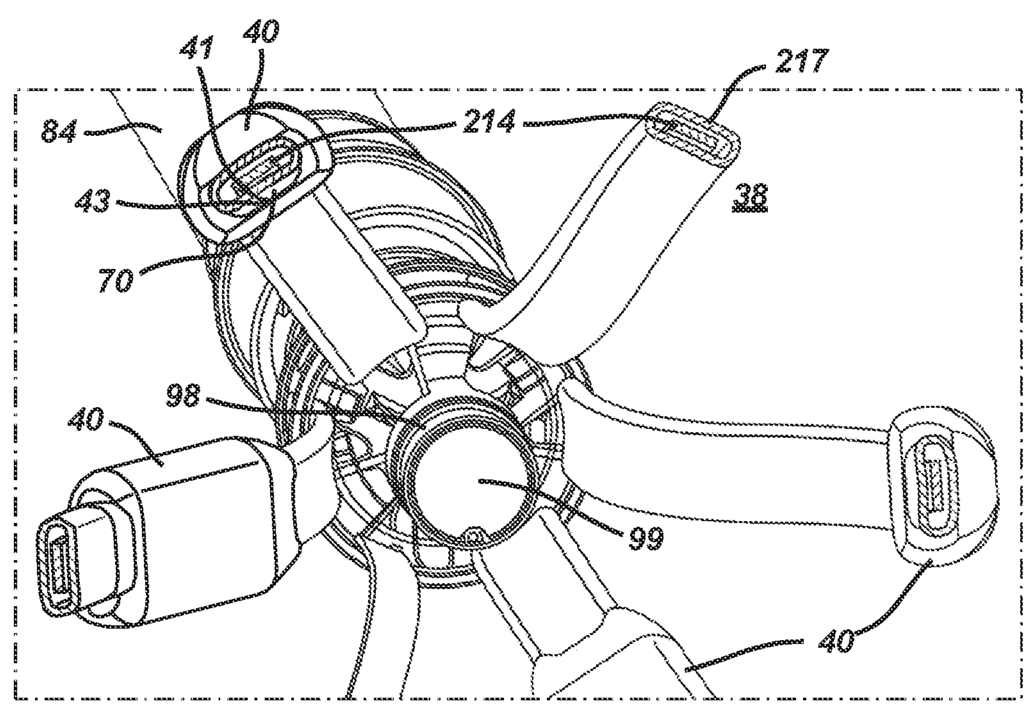
FIG. 2B is a sectional view of a cross-sectional plane orthogonal to axis 86 to show the internal components of electrode and spine assembly.

The medical probe 22 can include a guide sheath and a therapeutic catheter, wherein the guide sheath includes the flexible insertion tube 30 and the handle 32 and the therapeutic catheter includes the basket assembly 38, electrodes 40, and a tubular shaft 84 (see FIGS. 2A through 2B). The therapeutic catheter is advanced through the guide sheath so that the basket assembly 38 is positioned in the heart 26. The distal end 39 of the medical probe 22 corresponds to a distal end of the guide sheath when the basket assembly 38 is contained within the flexible insertion tube 30, and the distal end 39 (of the tube 30) corresponds to a proximal portion (FIG. 2A) of the basket assembly 38 when the basket assembly 38 is extended from the distal end of the guide sheath. The medical probe 22 can be alternatively configured to include a second handle on the therapeutic catheter and other features as understood by a person skilled in the pertinent art.

In the configuration shown in FIG. 1, control console 24 is connected, by a cable 42, to body surface electrodes, which typically include adhesive skin patches 44 that are affixed to patient 28. Control console 24 includes a processor 46 that, in conjunction with a tracking module 48, determines location coordinates of distal end 39 inside heart 26. Location coordinates can be determined based on electromagnetic position sensor output signals provided from the distal portion of the catheter when in the presence of a generated magnetic field. Location coordinates can additionally, or alternatively be based on impedances and/or currents measured between adhesive skin patches 44 and electrodes 40 that are affixed to basket assembly 38. In addition to being used for recording ECG signals or acting as location sensors during a medical procedure, electrodes 40 may perform other tasks such as ablating tissue in the heart.

As described hereinabove, in conjunction with tracking module 48, processor 46 may determine location coordinates of distal end 39 of tube 30 inside heart 26 based on impedances and/or currents measured between adhesive skin patches 44 and electrodes 40. Such a determination is typically after a calibration process relating the impedances or currents to known locations of the distal end has been performed. While embodiments presented herein describe electrodes 40 that are preferably configured to deliver IRE ablation energy to tissue in heart 26, configuring electrodes 40 to deliver any other type of ablation energy to tissue in any body cavity is considered to be within the spirit and scope of the present invention. Furthermore, although described in the context of being electrodes 40 that are configured to deliver IRE ablation energy to tissue in the heart 26, one skilled in the art will appreciate that the disclosed technology can be applicable to electrodes used for mapping and/or determining various characteristics of an organ or other part of the patient's 28 body.

Processor 46 may include real-time noise reduction circuitry 50 typically configured as a field programmable gate array (FPGA), followed by an analog-to-digital (A/D) signal conversion integrated circuit 52. The processor can be programmed to perform one or more algorithms and uses circuitry 50 and circuit 52 as well as features of modules to enable the medical professional 34 to perform the IRE ablation procedure.

Control console 24 also includes an input/output (I/O) communications interface 54 that enables control console 24 to transfer signals from, and/or transfer signals to electrodes 40 and adhesive skin patches 44. In the configuration shown in FIG. 1, control console 24 additionally includes an IRE ablation module 56 and a switching module 58.

IRE ablation module 56 is configured to generate IRE pulses including peak power in the range of tens of kilowatts. In some examples, the electrodes 40 are configured to deliver electrical pulses including a peak voltage of at least 900 volts (V). The medical system 20 performs IRE ablation by delivering IRE pulses to electrodes 40. Preferably, the medical system 20 delivers biphasic pulses between electrodes 40 on the spine. Additionally, or alternatively, the medical system 20 delivers monophasic pulses between at least one of the electrodes 40 and at least one skin patch.

In order to prevent blood coagulation, system 20 supplies irrigation fluid (e.g., a normal saline solution) to distal end 39 of tube 30 and to the proximal area of basket assembly 38. It is noted that irrigation fluid can be supplied through the flexible insertion tube 30. Control console 24 includes an irrigation module 60 to monitor and control irrigation parameters, such as the pressure and the temperature of the irrigation fluid. It is noted that while the preference for the exemplary embodiments of the medical probe is for IRE or PFA, it is within the scope of the present invention to also use the medical probe separately only for RF ablation (unipolar mode with an external grounding electrode or bipolar mode) or in combination with IRE and RF ablations sequentially (certain electrodes in IRE mode and other electrodes in RF mode) or simultaneously (groups of electrodes in IRE mode and other electrodes in RF mode).

Based on signals received from electrodes 40 and/or adhesive skin patches 44, processor 46 can generate an electroanatomical map 62 that shows the location of distal end 39 in the patient's body. During the procedure, processor 46 can present map 62 to medical professional 34 on a display 64, and store data representing the electroanatomical map in a memory 66. Memory 66 may include any suitable volatile and/or non-volatile memory, such as random-access memory or a hard disk drive.

In some embodiments, medical professional 34 can manipulate map 62 using one or more input devices 68. In alternative embodiments, display 64 may include a touchscreen that can be configured to accept inputs from medical professional 34, in addition to presenting map 62.

FIG. 2A is an illustration of a perspective view of a medical probe 22 including a basket assembly 38 in an expanded form when unconstrained, such as by being advanced out of an insertion tube lumen at a distal end 39 of an insertion tube 30. Probe 22 may include a contact force sensor 400 to determine contact force of the spines against cardiac tissues. Details of the contact force sensor are shown and described in US Patent Application Publication No. US20210077180A1 published Mar. 18, 2021, which disclosure is incorporated by reference herein.

It should be noted that the medical probe 22 illustrated in FIG. 2A lacks the guide sheath illustrated in FIG. 1. In the expanded form FIG. 2A, spines 214 bow radially outwardly and in the collapsed form (not shown) the spines 214 are arranged generally along a longitudinal axis 86 of insertion tube 30. In FIG. 2A, a plurality of electrically insulative jackets 217 is provided so that each jacket can be disposed between a respective spine 214 of the plurality of spines and a respective electrode 40 of the plurality of electrodes, thereby electrically isolating the plurality of electrodes from the plurality of spines.

Figure 3A:
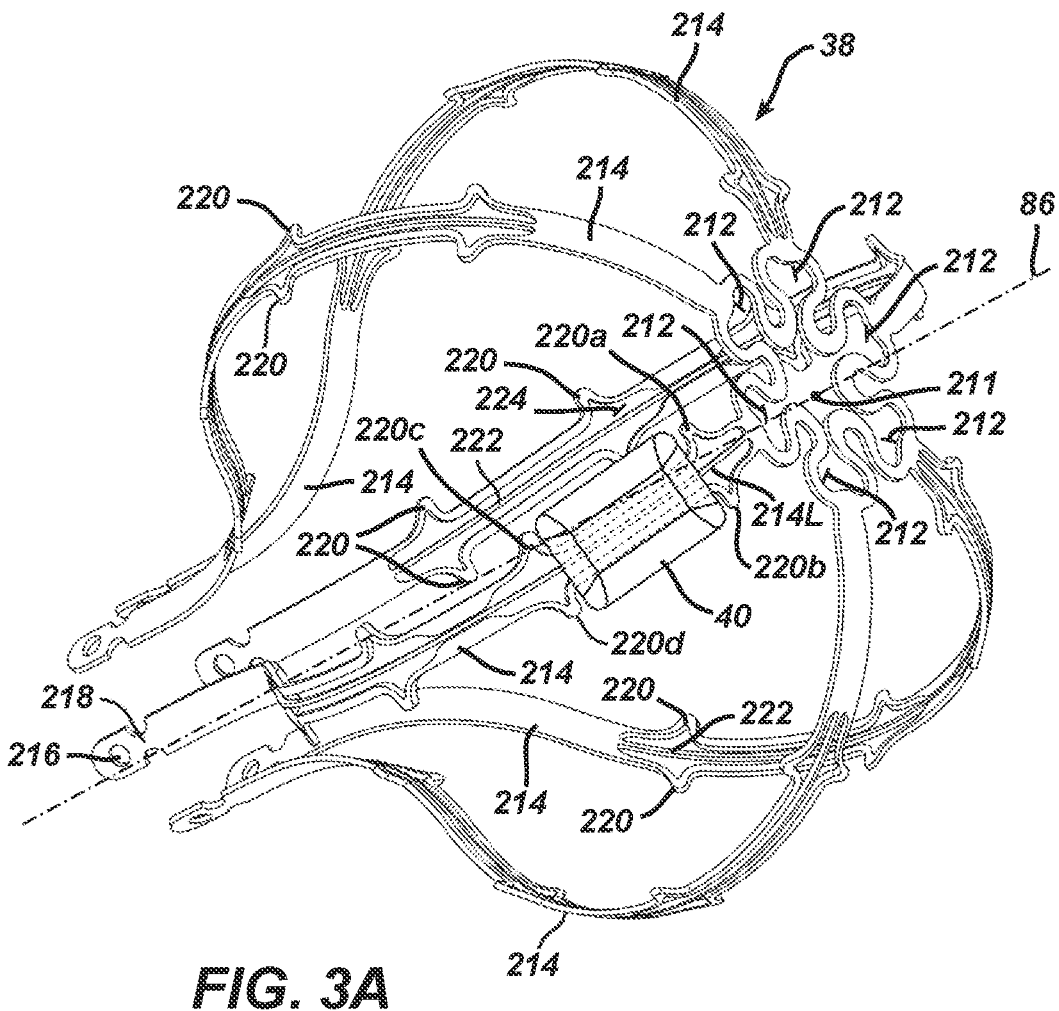
FIG. 3A illustrates the medical probe of FIG. 2A with only the underlying spine structure and one electrode disposed on one spine.

As shown in FIG. 2A, basket assembly 38 includes a plurality of flexible spines 214 that are formed at the end of a tubular shaft 84 and are connected at both ends. During a medical procedure, medical professional 34 can deploy basket assembly 38 by extending tubular shaft 84 from insertion tube 30 causing basket assembly 38 to exit insertion tube 30 and transition to the expanded form. Spines 214 may have elliptical e.g., circular, or rectangular that may appear to be flat cross-sections, and include a flexible, resilient material e.g., a shape-memory alloy such as nickel-titanium, also known as Nitinol forming a strut as will be described in greater detail herein. As shown in FIGS. 2A, 2B and 3A, basket assembly 38 has a proximal portion 36 and a distal end 39. The medical probe 22 can include a hub 90 that can function as a spine retention hub and/or an irrigation hub 90 that extends longitudinally from a distal end of tubular shaft 84 towards distal end 39 of basket assembly 38. As described supra, control console 24 includes irrigation module 60 that delivers irrigation fluid to basket assembly 38 through tubular shaft 84.

Turning to FIG. 3A, the plurality of flexible linear spines 214 converge at a central spine intersection 211 that is also disposed on a longitudinal axis 86 defined by the spines 214. In some examples central spine intersection 211 can include one or more cutouts 212 that allow for bending of the spines 214 when each spine respective attachment end 216 is connected to the spine retention hub 90, described in more detail below.

As shown herein, electrodes 40 positioned on spines 114 of basket assembly 38 can be configured to deliver ablation energy RF and/or IRE to tissue in heart 26. Additionally, or alternatively, the electrodes can also be used to determine the location of basket assembly 38 and/or to measure a physiological property such as local surface electrical potentials at respective locations on tissue in heart 26. The electrodes 40 can be biased such that a greater portion of the one or more electrodes 40 face outwardly from basket assembly 38 such that the one or more electrodes 40 deliver a greater amount of electrical energy outwardly away from the basket assembly 38 i.e., toward the heart 26 tissue than inwardly.

Examples of materials ideally suited for forming electrodes 40 include gold, platinum and palladium and their respective alloys. These materials also have high thermal conductivity which allows the minimal heat generated on the tissue i.e., by the ablation energy delivered to the tissue to be conducted through the electrodes to the back side of the electrodes i.e., the portions of the electrodes on the inner sides of the spines, and then to the blood pool in heart 26.

Referring to FIG. 3A, basket assembly 38 of medical probe 22 is shown without the insulative sleeve 217 or associated wirings to electrodes 40 being disposed inside sleeve 217 to show the novel underlying basket structure 38. Basket 38 includes a single unitary structure that includes a plurality of spines 214 formed from a cylindrical tube stock (FIG. 3B) and treated to cause the spines 214 to bias radially outward. The material for the spine 214 can be selected from a group consisting of nitinol, cobalt chromium, stainless steel, titanium, and combinations hereof.

Referring to FIG. 2A, the spine retention hub 90 can be inserted into the tubular shaft 84 and attached to the tubular shaft 84. Spine retention hub 90 can include a cylindrical member 94 including a plurality of relief lands 96, multiple irrigation openings 98 to allow outflow of irrigation fluid into a volume defined by the basket spines, and hub end 99. Relief lands 96 can be disposed on the outer surface of cylindrical member 94 and configured to allow a portion of each spine 214, such as each spine attachment end 216, to be fitted into a respective relief land 96 of retention hub 90 also known as a coupler for a contact force sensor 400. The attachment end 216 can be a generally linear end of the spine 214. The attachment end 216 can be configured to extend outwardly from the spine retention hub 90 such that the basket assembly 38 is positioned outwardly from the spine retention hub 90 and, consequently, outwardly from the tubular shaft 84. In this way, the spine 214 can be configured to position the basket assembly 38 distally from the distal end of the tubular shaft 84 and distal from the distal end of the insertion tube 30 when the basket assembly 38 is deployed. Reference electrode 95 can be disposed on the projection 94 or on the hub end surface 99. It should be noted that hub 90 in effect can have multiple functions: (1) to retain the spine legs proximally; (2) allow hub 90 (as well as the basket assembly 38) to be connected to distal tube 84; (3) to function as a fluid diverter for irrigation fluid delivered through distal tube 84; and (4) provide a reference electrode 95.

Figure 2C:
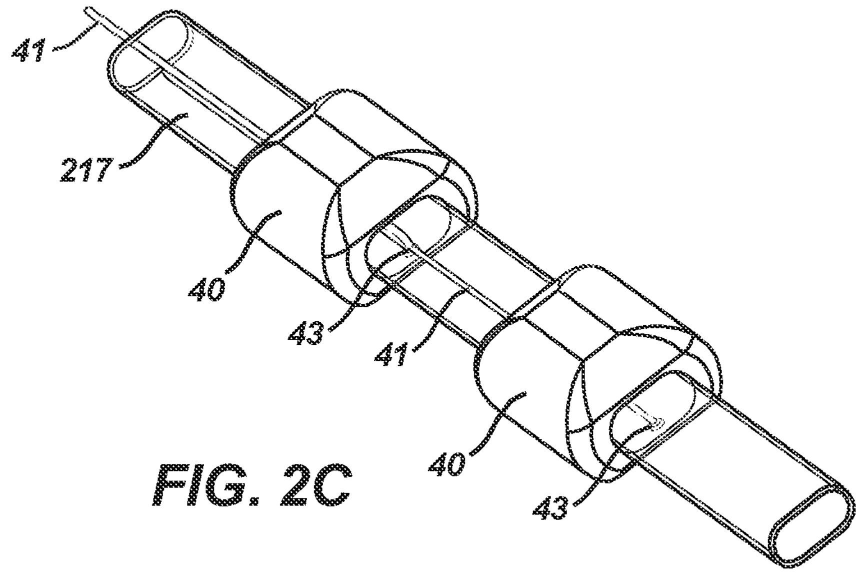
FIG. 2C is a perspective view of electrodes mounted on the insulative jacket with wires running along a spine for connection to each electrode.

Referring to FIG. 2B, a sectional view of the spines and electrodes are shown cut-away to show the spine frame 214 disposed inside jacket 217 with wiring 41 running along the spine frame 214 and extending through the jacket 217 to connect with the electrode 40 via connection point (e.g., solder pad) 43. FIG. 2C shows a perspective view of an opaque jacket 217 through which wirings 41 can be seen to extend through jacket to respective connection points 43 of electrodes 40. It should be noted that the connection point 43 is not required to be disposed inside the lumen 70 of electrode 40 but can be outside lumen 70 as long as the connection point does not interfere with tissue contact of the electrode 40.

Figure 6A:
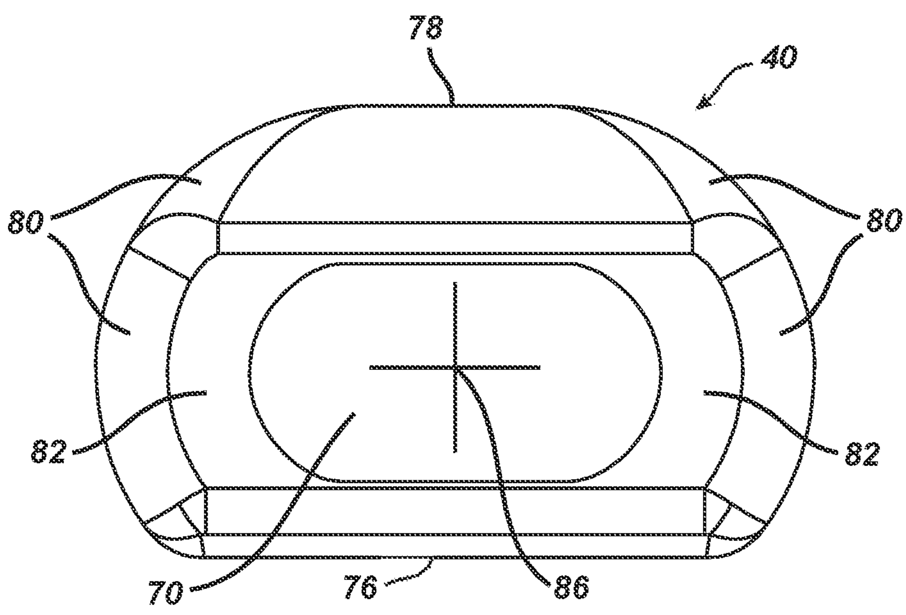
FIG. 6A and FIG. 6B are a close-up view showing an electrode.
Figure 6B:
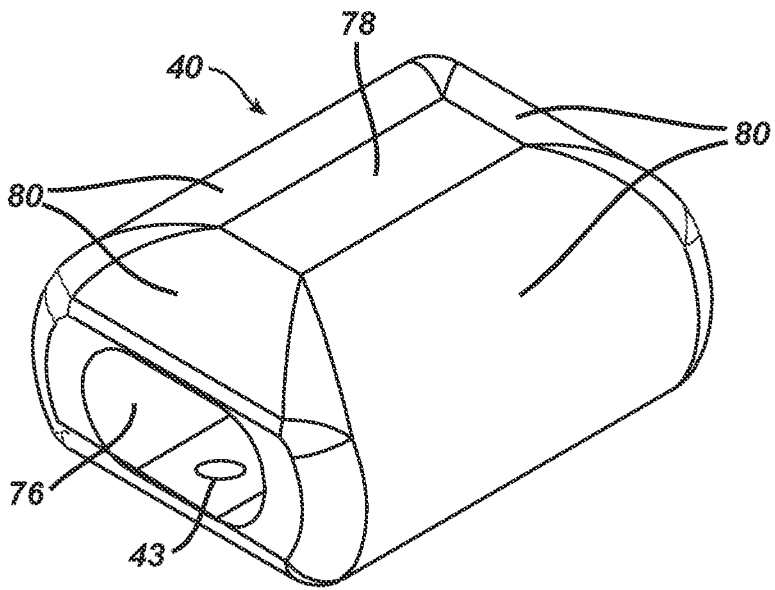

Referring to FIGS. 6A and 6B, in a preferred embodiment, electrode 40 is about 2 mm to about 3 mm long with a width from about 1.5 mm to about 2.5 mm wide and a height of about 0.8 mm to about 1.5 mm. The lumen 70 may have a negative surface area of about 0.4 mm-squared to about 0.7 mm-squared. The lumen 70 is not placed at the geometrical center but is rather offset lower so that the center 86 of lumen 70 is more towards the flat bottom surface 76. This arrangement ensures that more of the top surfaces 78 and 80 of electrode 40 is above the lumen 70 than below lumen 70.

Referring to FIG. 3A, electrode 40 can be located substantially in place with respect to spine 214 by way of a retention member 220 formed integrally with the spine 214. As illustrated in FIG. 3A, each of the spines 214 can include at least one retention member 220 extending generally transverse to the spine 214. To allow for insertion of the spine 214 through lumen 70 (FIG. 6A) of electrode 40, each spine 214 can be bisected with a central spine member 222 so that empty space 224 is provided to allow retention member 220 to bend inwardly towards the central spine member 222. The shape of retention member 220 can be of any shape as along as such shape serves to allow the member 220 to be compressed for insertion into lumen 70 of electrode 40 and once released to prevent movement of electrode 40 with respect to the retention member 220. In one embodiment, the at least one retention member 220 is shaped in a bow-like configuration with a center of such bow extending away from a periphery of spine 214. In a preferred embodiment, the at least one retention member 222 for each electrode 40 may include two bow shaped members 220 disposed in opposite direction and transverse to a longer length 214L of each spine 214.

In the configuration shown in FIG. 3A, the at least one retention member may have first 220*a*, 220*b* and second sets 220*c*, 220*d* of retention members 220 spaced apart along the spines. The first set includes two bow shaped members 220*a*, 220*b* disposed in opposite direction and transverse to a longer length 214L of each spine 214 and the second set includes two bow shaped members 220*c*, 220*d* disposed in opposite direction and transverse to a longer length 214L of each spine 214 so that each electrode 40 is captured between the first and second sets of retention members 220*a*, 220*b* and 220*c* and 220*d*.

Figure 3B:
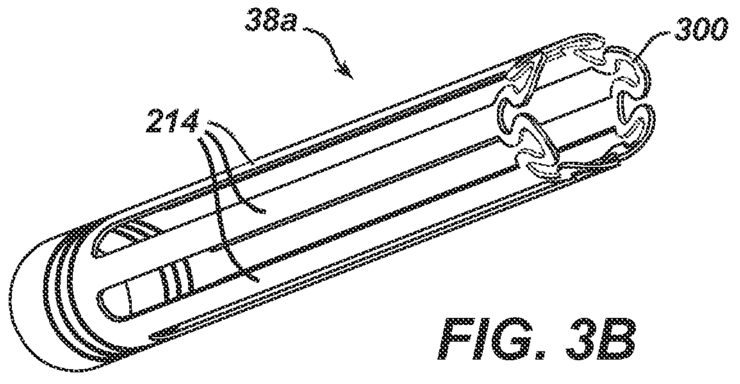
FIG. 3B illustrates the spine structure as formed from a tube stock.

FIG. 3B shows the spine structure 38*a* as formed from a tube stock. It is also within the scope of this invention for the spine structure 38*a* to be formed form a flat sheet stock, cut and heat treated to achieve the spheroidal basket shape shown herein. The spine structure 38*a* illustrated in FIG. 3B can be compressed longitudinally and the spines 214 can expand radially to form the basket shape spine structure illustrated in FIG. 3A of basket assembly 38 illustrated in FIG. 2A.

Figure 4A:
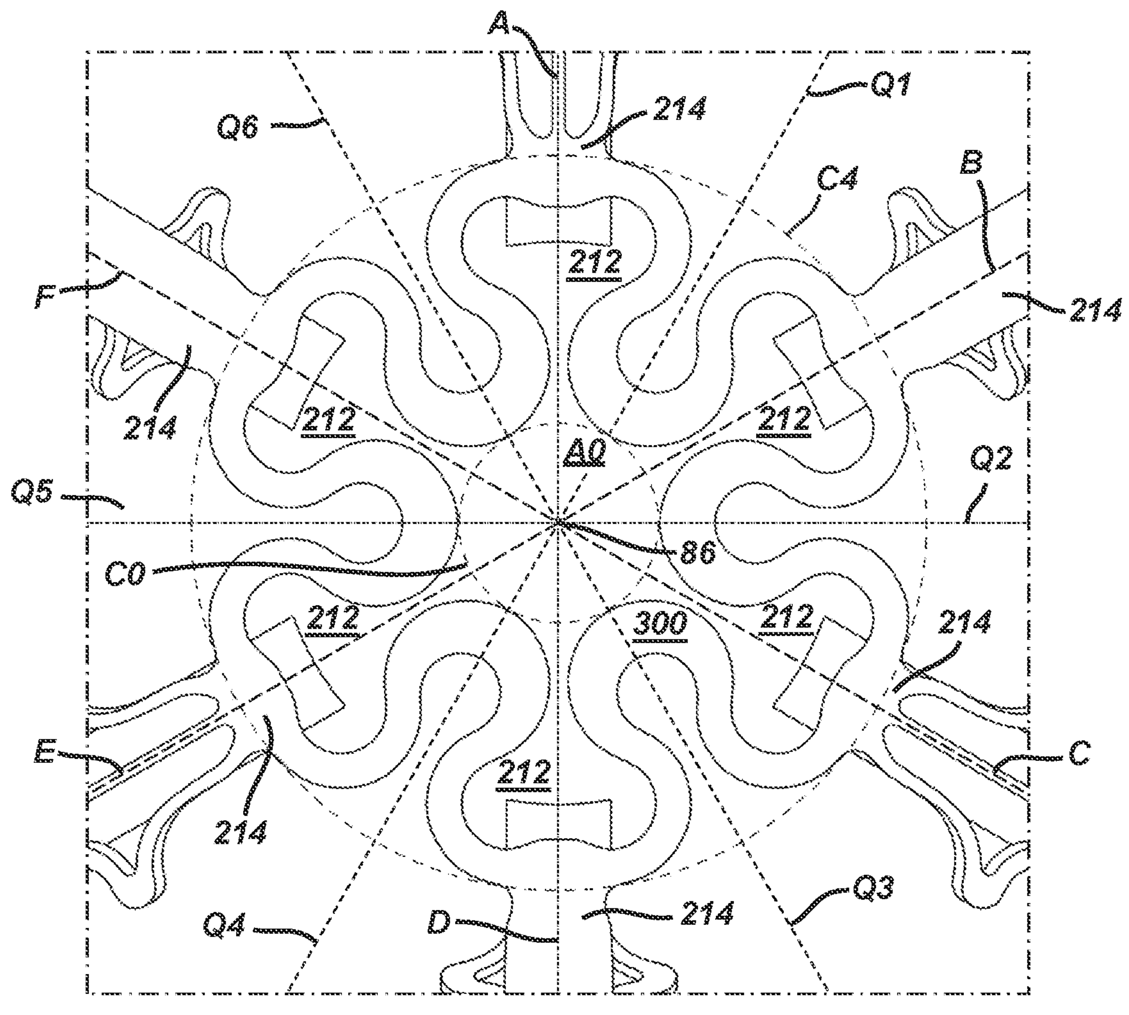
FIG. 4A illustrates an end and flattened view of the distal end of the basket spine structure of FIG. 3A as if the entire basket spines are captured flat between two flat plates of glass for viewing by an observer located on the longitudinal axis.
Figure 4B:
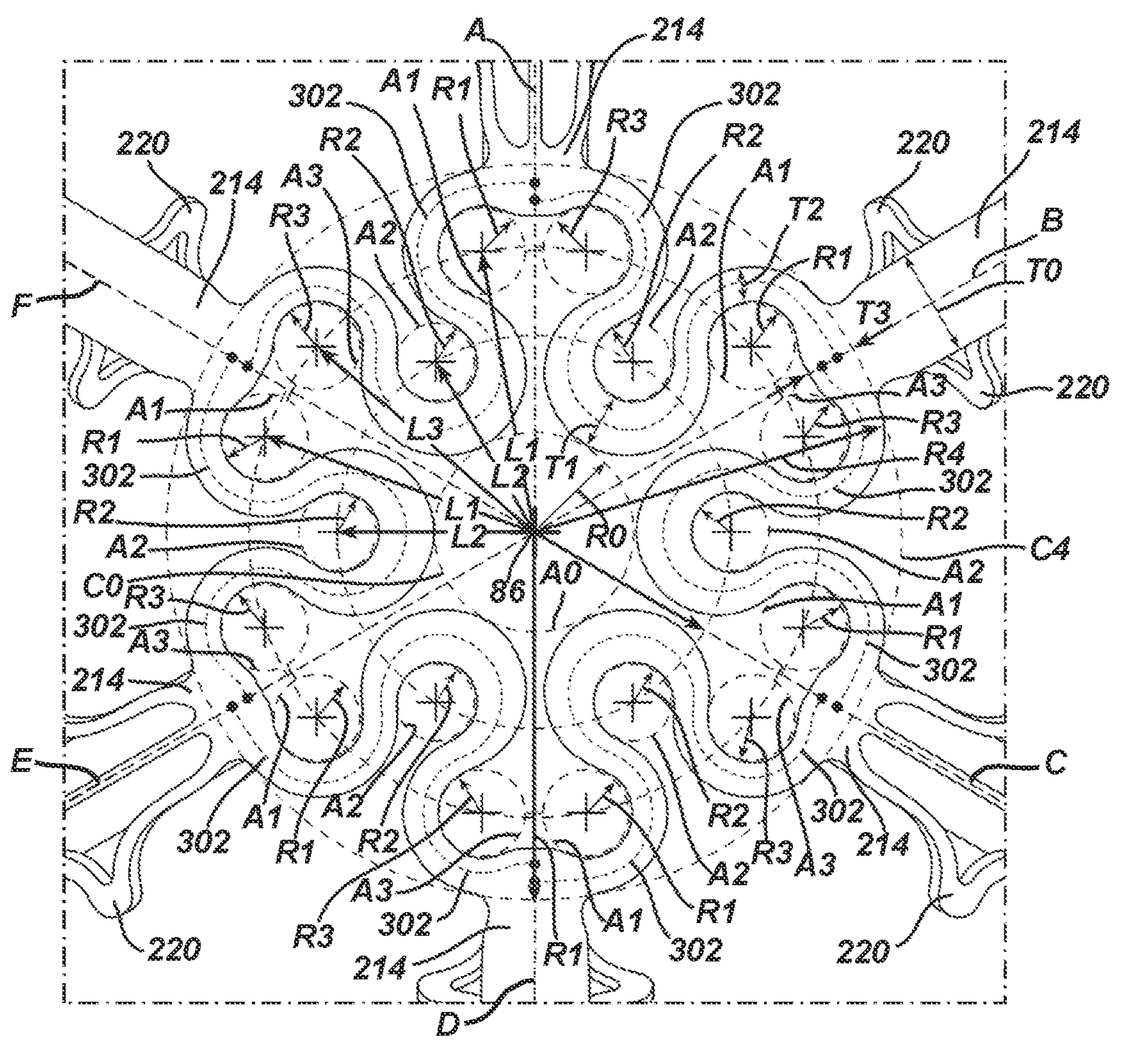
FIG. 4B illustrates the end view of the spine structure of FIG. 4A with design nomenclatures of a cloverleaf structure disposed proximate the distal end of the spine structure of FIG. 3A.

FIGS. 4A and 4B show the distal portion 39 (FIG. 2A) in which the distal portion 39 of basket assembly 38 of medical probe 22 can be considered as being flattened between two flat sheets of glass. In this viewing configuration, it can be seen in FIG. 4A that distal portion 39 defines a structure 300 resembling a cloverleaf and hence structure 300 will be referred hereafter as a "cloverleaf". As before, basket 38 in FIG. 4A and FIG. 4B has a plurality of spines 214 extending along the longitudinal axis 86 from a proximal central proximal spine portion 36 to a distal spine portion 39.

In FIG. 4A, the distal spine portion 39 defines a cloverleaf structure FIG. 4A, 300 disposed radially around the longitudinal axis 86. Each clover cutout 212 is aligned along radial axis A, B, C, D, E and F extending orthogonally from axis 86 so that the plurality of spines 214 extend from the proximal central spine portion 36 in an equiangular pattern such that respective angles between respectively adjacent spines are approximately equal. While the preferred embodiment includes six spines, it is within the scope of the invention to have any number of spines from four to twelve.

Of note is that the cloverleaf structure 300 also defines a central cutout CO with a negative or empty area A0 disposed about the longitudinal axis 86. In particular, the cloverleaf structure 300 can be delineated by the following structures: a sinusoidal-like cloverleaf member 300 extending from one spine 214 to an adjacent spine 214 in a direction e.g., counterclockwise, or clockwise around the longitudinal axis 86. This characteristic of the sinusoidal structure 300 can be seen in FIG. 4B with for example, spine 214 located on radial axis A. Starting from this spine 214 on axis A, a sinusoidal-like cloverleaf member 300 is configured so that it meanders as indicated by dashed line 302 around a portion of the cutout 212 having a negative or open first area A1 which can be approximated by circle R1. As used herein, the term "open area" means the absence of any solid structure to define an empty space. This first open area A1 is approximately 20% that of the central area A0. For convenience, the first open area A1 can be approximated by the first virtual circle R1 that has its center located at a first distance L1 to the longitudinal axis 86. Continuing in FIG. 4B, the sinusoidal cloverleaf member 300 meanders in a counter-clockwise direction from axis A to axis F around a second open area A2 towards an adjacent spine 214 located on axis F. For convenience, the second open area A2 can also be approximated to a second virtual circle R2 having a second open area A2 of approximately 90% of the first open area A1. It is noted that the second virtual circle may have its center of radius R2 located at a second distance L2 smaller than the first distance L1 to the longitudinal axis 86. Continuing towards axis F in FIG. 4B, the sinusoidal cloverleaf member 300 meanders dashed line 302 around a third open area A3 which for convenience is approximated by third virtual circle with radius R3. The third virtual circle has its center for radius R3 located at a third distance L3 to the central axis 86 that is greater than L2 and approximately equal to the first distance L1. Once the sinusoidal cloverleaf member 300 crosses axis F, the structural nomenclatures repeat again with another first open area A1 on the other side of axis F closer to axis E on which sinusoidal cloverleaf member 300 meanders as referenced by dashed line 302 towards next spine 214 located on axis E.

In FIG. 4B, a width T0 of the spine 214 can be from 0.25 to 1 mm while the sinusoidal member 302 has a maximum width T1 of about ½ of the width of T0 with a minimum width T2 of about ⅓ of spine width T0. A width T3 proximate the spine axis (A, B, C, D, E or F) is about the same as the maximum with T1. The central area A0, approximated by radius R0, is approximately 0.8 mm-squared, the fourth virtual circle C4 may have an area approximately 14 times greater than the central area A0. Each of the first and third virtual circle R1 and R3 is located at a first distance L1 of approximately 1.5 mm from the central axis 86 while the second virtual circle R2 is located at a distance L2 of approximately ½ that of the first distance L1.

Preferably, the plurality of spines 214 can be made from a material selected from a group consisting of nitinol, cobalt chromium, stainless steel, titanium, and combinations or alloys hereof. Each electrode 40 can be made of a material selected from stainless steel, cobalt chromium, gold, platinum, palladium, and alloys or combinations hereof.

The inventors have devised the cloverleaf structure 300 in order to allow the basket assembly 38 to be compressed from a maximum diameter of the basket of approximately 12 mm to fit within an 8-12 French sheath without buckling or causing permanent plastic deformation to the spines 214 at any part of the basket assembly 38. In an alternative embodiment, if the number of spines is increased the size of the sheath may be increased to up to 14.5 French to accommodate the additional spines. By virtue of this design, the inventors have been able to compress the basket into a sheath and deploy for full expansion for at least 40 times without any physical sign of buckling.

Referring back to FIG. 4A, it is noted that the sinusoidal-like cloverleaf member 300 is configured so that a portion of cloverleaf member 300 is tangential to the central circle CO proximate a location between any two radial axes on which two neighboring spines 214 are located. For example, with spine 214 on radii axis A neighboring spine 214 on axis B, the sinusoidal cloverleaf member 300 is tangential to the open circle CO at a location bisecting the two radial axis A and B by a line Q1 connected to the central axis 86. This tangential characteristic of the sinusoidal cloverleaf member 300 around the open area A0 is repeated for any two adjacent spines 214 as spine 214 on axis B and spine 214 on axis C and so on for all of the bisecting axes Q1, Q2, Q3, Q4, Q5, Q6. The bisecting axes Q1, Q2, Q3, Q4 correspond to peaks of the sinusoidal cloverleaf member 300 and the radial axes A, B, C, D, E, F correspond to troughs of the sinusoidal cloverleaf, wherein peaks of the sinusoidal member are closer to the central axis 86 and troughs are further from the central axis 86.

Figure 5A:
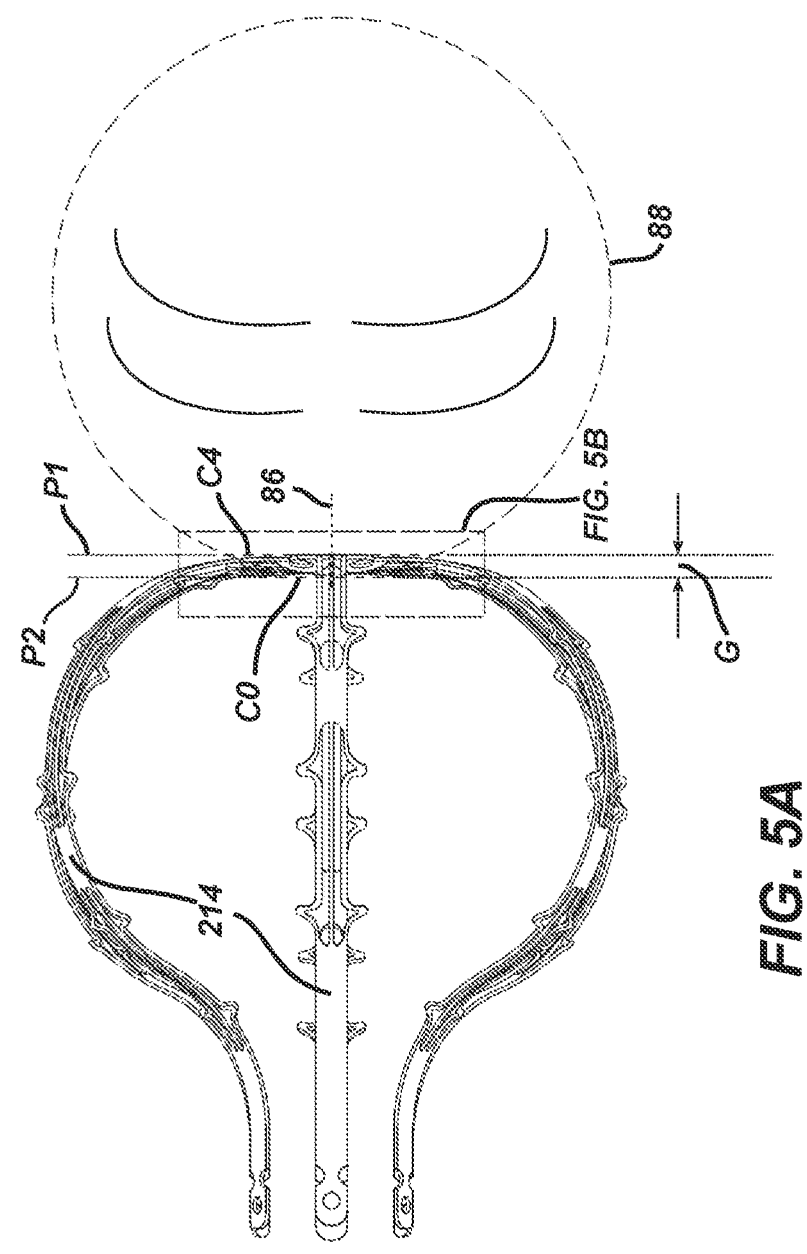
FIG. 5A illustrates a side view of the basket spine structure of FIG. 3A to illustrate a concavity of the cloverleaf structure that can be approximated by a virtual sphere.
Figure 5B:
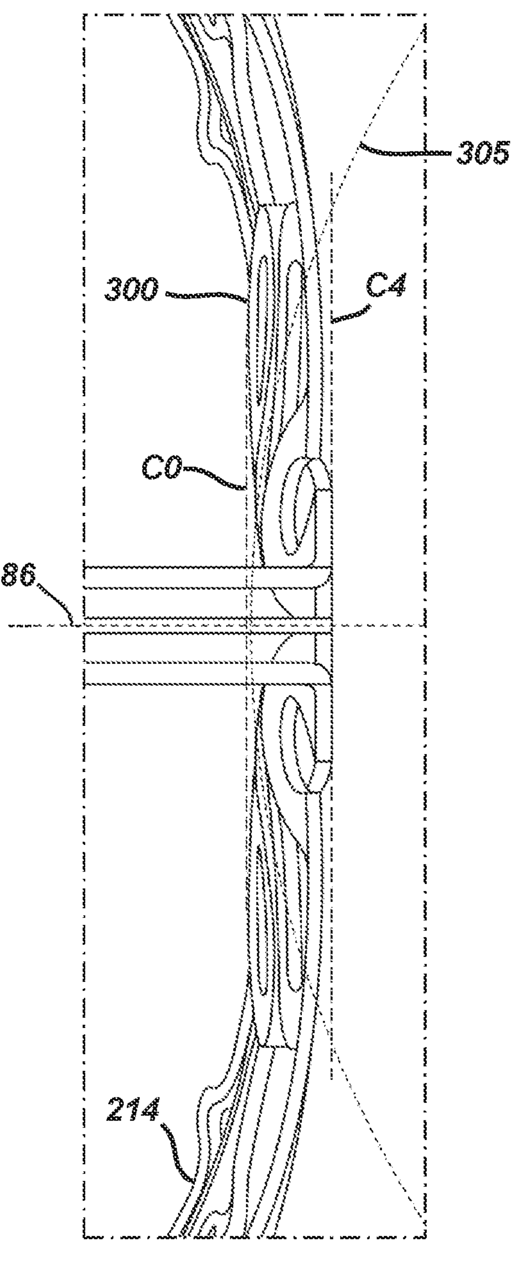
FIG. 5B is a close-up of the inset shown in FIG. 5A to show the concavity of the distal central portion of basket assembly 38.

Another notable feature of the basket structure 38 is a concavity 305 of the distal central portion 211 (FIG. 3A) that can be seen with reference to FIGS. 5A and 5B. In FIG. 5A, it can be seen that the cloverleaf structure 300 is bent so that its open center 211 is contiguous to a plane defined by central circle CO and spaced apart by a gap G with respect to a plane defined by the fourth virtual circle C4 encircling the cloverleaf structure 300. The concavity is indicated by dashed line 305 representing the compound curvature generated by the cloverleaf structure 300 about the central axis 86.

FIG. 6A illustrates the electrode 40 an end front view and FIG. 6B illustrates the same electrode from a top-down perspective view of electrode 40, in accordance with an embodiment of the present invention. Each electrode 40 is fabricated from a biocompatible electrically conductive material, such as stainless steel, cobalt, chromium, platinum, palladium, iridium or gold and alloys or combinations of such metals. Each end (one shown in FIG. 6A) of electrode 40 is provided with generally flat lands 82 surrounding a lumen 70 with curved outer surfaces 80 surrounding the lands 82. Electrode 40 has a tissue facing surface with a generally flat top surface 78 with curved outer perimeter 80 surrounding the generally flat top surface 78. The lumen 70 (i.e., a hollow through opening) extends along longitudinal axis 86 therethrough. In addition to the tissue contacting outer surface, each given electrode 40 has an inner surface 76 defined by its lumen 70 on which spine 214 can be inserted through the lumen 70. Electrical wire or electrical trace 41 (FIG. 2C, sufficiently sized to deliver current pulses of at least 10 amps) can be connected to a connection point on the electrode (outside or inside surface). Preferably, wire 41 is electrically connected to a connection point 43 on the inside surface 76 of lumen 70. The cross-section of the electrode can be ovoid, trapezoidal, or substantially ovoid or trapezoidal shape as shown in FIGS. 6A and 6B.

Figure 7A:
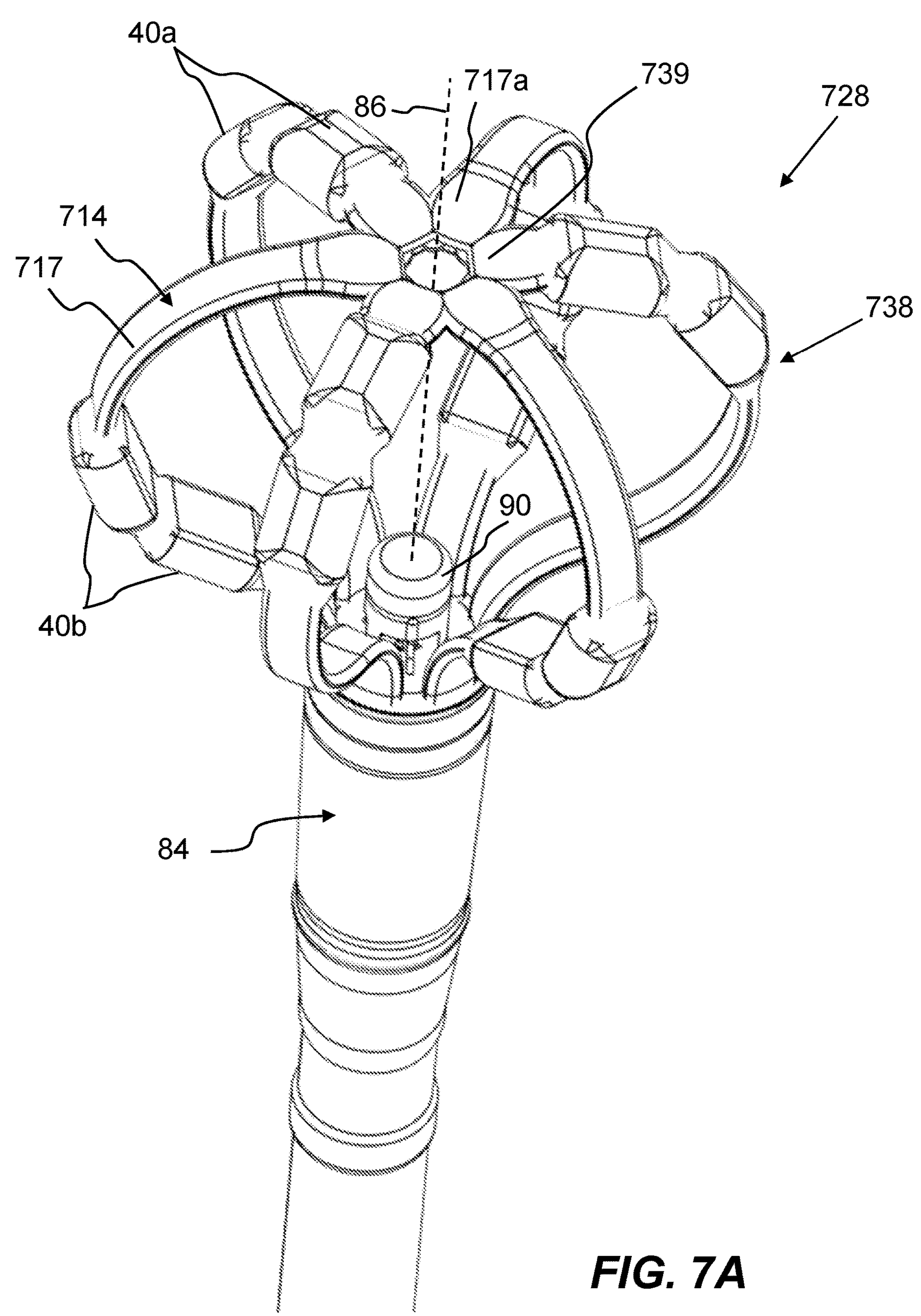
FIG. 7A is a schematic pictorial illustration showing a perspective view of another example medical probe with electrodes in an expanded form, in accordance with another example of the disclosed technology.
Figure 7B:
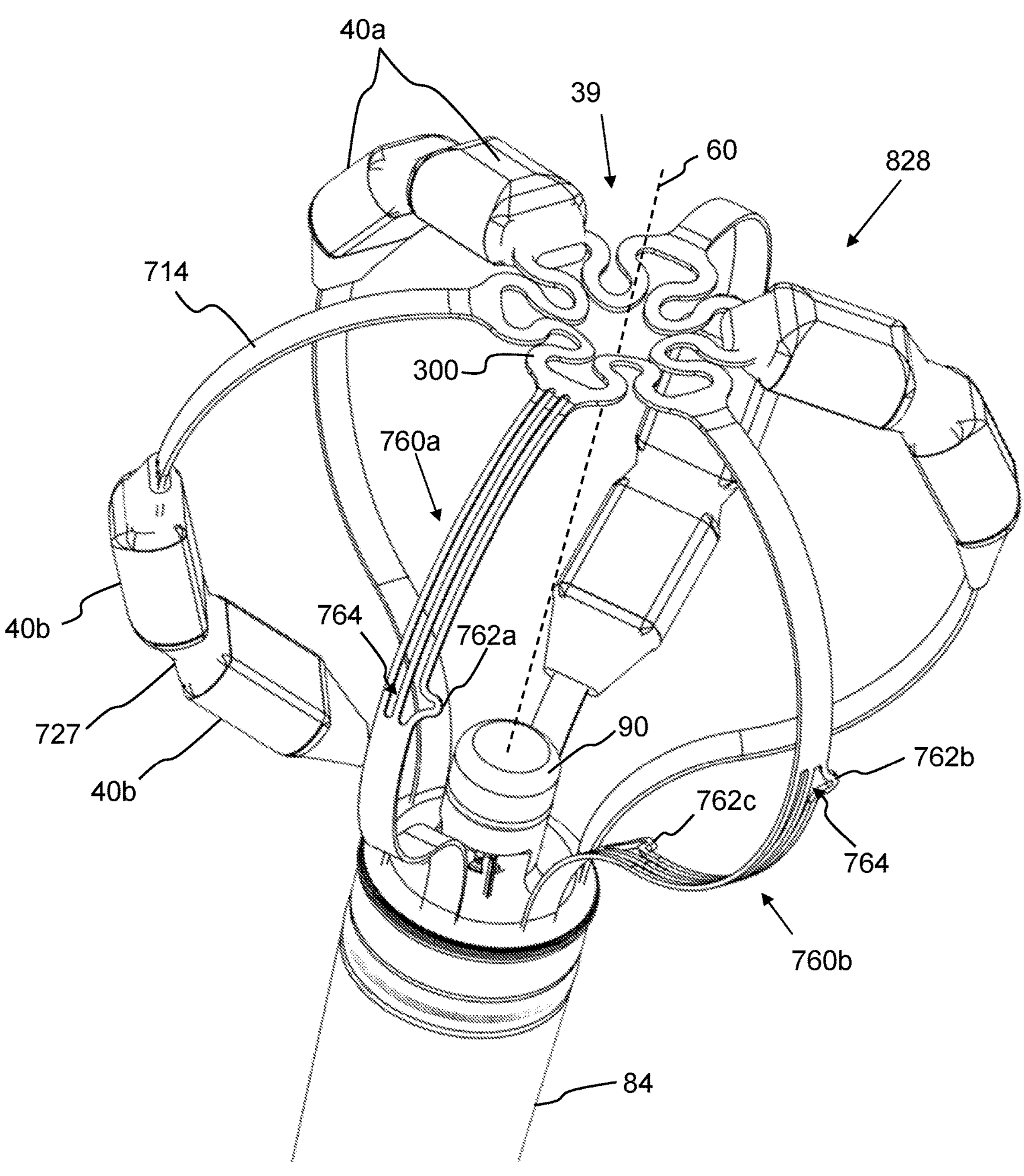
FIG. 7B is a schematic pictorial illustration showing a perspective view of the medical probe of 8A showing the spines, in accordance with the disclosed technology.

FIGS. 7A and 7B illustrate another example basket catheter 728 with a basket assembly 738 having a plurality of electrodes 40*a*, 40*b* disposed on spines 714 and a hub 90 that can function similarly to the hub 90 illustrated in FIGS. 2A and 2B. As shown in FIG. 7A, the electrodes 40*a*, 40*b* can be disposed in alternating groupings of distal electrodes 40*a* and proximal electrodes 40*b* on adjacent spines 714. For example, and as shown in FIGS. 7A and 7B, two electrodes 40*a*, 40*b* can be disposed on the spines 714 close to each other with no additional electrodes 40*a*, 40*b* disposed on the same spine 714. On a first spine 714, the two electrodes 40*b* can be disposed together near the proximal end of the spine 714 while on a second, adjacent spine 714 two electrodes 40*a* can be disposed together near the distal end of the adjacent spines 714. In this way, the electrodes 40*a*, 40*b* can be offset around the circumference of the basket catheter 728 such that the basket assembly 738 is better able to collapse when retracted into a sheath. When the basket assembly 738 is collapsed, the distal electrodes 40*a* are positioned entirely in a distal direction from the proximal electrodes 40*b* with a gap along the longitudinal axis 86 between the proximal electrodes 40*b* and the distal electrode 40*a*.

With the configuration of electrodes 40*a*, 40*b* disposed on the spines 714 as shown in FIGS. 7A and 7B, the system 10 (FIG. 1) can be configured to output bipolar high-voltage DC pulses as may be used to effect irreversible electroporation (IRE) between the two adjacent electrodes 40*a*, 40*b* on a given spine 714, electrically connect the two adjacent electrodes 40*a*, 40*b* on a given spine 714 and output bipolar high-voltage DC pulses between one or more electrodes 40*a*, 40*b* on another one of the spines 714 of the basket assembly 738, and/or output monopolar high-voltage DC pulses between one or more of the electrodes 40*a*, 40*b* and the one or more electrode patches 44 (FIG. 1) disposed on the skin of a patient 28. The two electrodes 40*a*, 40*b* on a given spine 714 can include an insulative material 727 disposed between the two electrodes 40*a*, 40*b*, thereby electrically isolating the two electrodes 40*a*, 40*b* in an electrode pair from each other.

The spines 714 can be covered with an insulative liner or jacket 717 that can be disposed between the electrodes 40*a*, 40*b* and the frame of the spines 714. The insulative liner 717 can electrically isolate the electrodes 40*a*, 40*b* from the frame of the spines 714 to prevent arcing or shorting to the frame of the spines 714. The insulative liner 717 can extend from the hub 90 to the distal end 39 of the basket assembly 738.

FIG. 7B is an illustration of the basket assembly 738 with the insulative liners 717, a pair of distal electrodes 40*a*, and a pair of proximal electrodes 40*b*, and other spine elements removed, for the sake of illustration, so that the frame of the basket assembly 738 is visible. The spines 714 extend from the hub 90 and are joined together approximate a distal end 39 of the basket assembly 738 by a cloverleaf structure 300. The cloverleaf structure 300 can be configured similar to as disclosed in greater detail elsewhere herein, or a variation thereof. The insulative liner 717 can include flared ends 717*a* (FIG. 7A) that extend over a majority of the cloverleaf structure 300 (FIG. 7B) and may provide an atraumatic distal surface at the distal end 39 of the basket assembly 738. In this way, the insulative liner, or jacket 717 may prevent the frame of the basket assembly 738 from causing injury to tissue.

As illustrated in FIG. 7B, the spines 714 can further include an electrode retention region 760*a*, 760*b* that is configured to prevent an electrode 40*a*, 40*b* from sliding proximally or distally along the spine 714. Adjacent spines 714 can have spine retention regions 760*a*, 760*b* alternating between a proximal position and a distal position along the spine 714. That is, a first spine 714 can have an electrode retention region 760*b* disposed near a proximal end of the spine 714 and an adjacent spine 714 can have an electrode retention region 760*a* disposed near a distal end of the spine 714.

Each electrode retention region 760*a*, 760*b* can include one or more cutouts 764 that can permit the spine 714 to be bent or pinched inwardly. Each electrode retention region 760*a*, 760*b* can further include one or more retention members 762*a-c* that protrude outwardly and can be configured to prevent the electrode 40*a*, 40*b* from sliding proximally or distally along the spine 714. During manufacture, proximal ends of the frame of the basket assembly 738 are inserted into lumens of the electrodes 40*a*, 40*b*, and the electrodes 40*a*, 40*b* are slid distally along the spines 714 to their respective final position. The cutouts 764 permit the electrodes 40*a*, 40*b* to slide over a retention members 762*a-c*. Because of the one or more cutouts 764 in the spines 714, the retention members 762*a-c* can be configured to move inwardly when the spine 714 is pinched inwardly to permit an electrode 40*a*, 40*b* to slide over the retention member 762*a-c*. Once the electrode 40*a*, 40*b* is slid past the retention member 762, the retention member 762 can resiliently bend back to its previous position, thereby preventing the electrode 40*a*, 40*b* from sliding proximally or distally along the spine 714.

The proximal electrode retention region 760*b* includes a proximal retention member 762*c* and a distal retention member 762*b*. The proximal electrode retention region 760*b* need not be configured to permit the proximal electrodes 40*b* to pass over the distal retention member 762*b*. The distal electrode retention region 760*a* utilizes the cloverleaf structure 300 to prevent the distal electrodes 40*a* from moving distally once the distal electrodes 40*a* are in their respective final position.

Although the basket catheter 728 is shown as having two electrodes 40*a*, 40*b* disposed near each other on a given spine 714 and having alternating groupings of electrodes 40*a*, 40*b* on adjacent spines 714, the disclosed technology can include other configurations of electrodes and spines not shown. For example, the disclosed technology can include groupings of three or more electrodes and/or multiple groupings of electrodes disposed on spines, and may further include differing numbers of spines. Thus, the disclosed technology is not limited to the particular configuration of electrodes and spines shown and described herein.

The embodiments described above are cited by way of example, and the present invention is not limited by what has been particularly shown and described hereinabove. Rather, the scope of the invention includes both combinations and sub combinations of the various features described and illustrated hereinabove, as well as variations and modifications thereof which would occur to persons skilled in the art upon reading the foregoing description and which are not disclosed in the prior art.

The following clauses list non-limiting embodiments of the disclosure:

Clause 1. A medical probe, comprising: a tubular shaft including a proximal end and a distal end, the tubular shaft extending along a longitudinal axis of the medical probe; and an expandable basket assembly coupled to the distal end of the tubular shaft, the basket assembly comprising: a plurality of spines extending along the longitudinal axis from a proximal central spine portion to a distal spine portion, the distal spine portion defining a cloverleaf structure disposed radially around the longitudinal axis, the cloverleaf structure defining a central cutout with a central area disposed about the longitudinal axis, the cloverleaf structure comprising: a sinusoidal-like member extending from one spine to an adjacent spine in a direction around the longitudinal axis, the sinusoidal-like member meanders around: (a) a first virtual circle having a first open area of approximately 20% that of the central area, the first virtual circle having its center located at a first distance to the longitudinal axis, (b) a second virtual circle having a second open area of approximately 90% of the first open area, the second virtual circle having its center located at a second distance smaller than the first distance to the longitudinal axis, and (c) a third virtual circle having its third open area approximately equal to the first open area, the third virtual circle having its center located at a third distance approximately equal to the first distance to the longitudinal axis.

Clause 2. The medical probe according to clause 1, wherein the central area comprises approximately 0.8 mm-squared area, a fourth virtual circle encircling the sinusoidal-like member comprises an area approximately 14 times greater than the central area and each of the first and third virtual circle is located at a first distance from the longitudinal axis while the second virtual circle is located at a second distance of approximately ½ that of the first distance.

Clause 3. The medical probe according to clause 2, in which the sinusoidal-like member is tangential to the central circle.

Clause 4. The medical probe according to any one of clauses 1-3, wherein a cross-sectional shape of each electrode comprises a substantially ovoid or trapezoidal shape.

Clause 5. The medical probe according to any one of clauses 1-4, wherein each of the spines includes at least one retention member extending generally transverse to the spine.

Clause 6. The medical probe of clause 5, in which each electrode comprises a body defining a hollow portion extending through the body of the electrode so that a spine can be inserted into the hollow portion and retained by the at least one retention member.

Clause 7. The medical probe of clause 5, in which the at least one retention member comprises a bow shaped member.

Clause 8. The medical probe of clause 5, in which the at least one retention member comprises two bow shaped members disposed in opposite direction and transverse to a longer length of each spine.

Clause 9. The medical probe of clause 5, in which the at least one retention member comprises first and second sets of retention members spaced apart along the spines, the first set includes two bow shaped members disposed in opposite direction and transverse to a longer length of each spine and the second set includes two bow shaped members disposed in opposite direction and transverse to a longer length of each spine so that each electrode is captured between the first and second sets of retention members.

Clause 10. The medical probe according to any of clauses 1-5, wherein the plurality of spines extends from the proximal central spine portion in an equiangular pattern such that respective angles between respectively adjacent spines are approximately equal.

Clause 11. The medical probe according to any of clause 1-6, further comprising a plurality of electrically insulative jackets each disposed between a respective spine of the plurality of spines and a respective electrode of the plurality of electrodes, thereby electrically isolating the plurality of electrodes from the plurality of spines.

Clause 12. The medical probe according to clause 1, wherein each respective spine of the plurality of spines comprises two electrodes.

Clause 13. The medical probe according to any of clauses 1-11, further comprising a wire disposed inside the insulative jacket.

Clause 14. The medical probe according to clause 12, wherein the wire is electrically connected to one of the electrodes.

Clause 15. The medical probe according to any of clauses 1-14, wherein the plurality of spines comprise a material selected from a group consisting of nitinol, cobalt chromium, stainless steel, titanium, and combinations hereof.

Clause 16. The medical probe according to any of clauses 1-17, wherein each electrode comprises of a material selected from stainless steel, cobalt chromium, gold, platinum, palladium, and alloys hereof.

Clause 17. The medical probe according to any of the previous clauses, further comprising: a plurality of electrodes configured to deliver electrical pulses for irreversible electroporation, the pulses including a peak voltage of at least 900 volts (V).

Clause 18. The medical probe according to any of the previous clauses, wherein the plurality of spines is configured to form an approximately spherically-shaped basket assembly when in the expanded form.

Clause 19. The medical probe according to any of the previous clauses, wherein the plurality of spines is configured form an approximately oblate-spheroid basket assembly when in the expanded form.

Clause 20. The medical probe according to any of the previous clauses, further comprising irrigation ports disposed in the proximal portion of the basket to deliver an irrigation fluid to the plurality of electrodes.

Clause 21. The medical probe according to any of the previous clauses, in which the central cutout approximates a central circle with a central area and wherein the cloverleaf structure is disposed within a fourth circle with its center on the longitudinal axis so that portions of the cloverleaf close to the center circle is spaced apart along the longitudinal axis with respect to portions of the cloverleaf close to the fourth circle thereby defining a concave cloverleaf structure.

Clause 22. The medical probe according to any of the previous clauses in which the cloverleaf structure is concave with its center extending towards the proximal central spine portion of the basket to approximate a concave surface disposed about the longitudinal axis.

Clause 23. The medical probe of any of the previous clauses in which a reference electrode is disposed proximate the distal end of the tubular shaft.

Clause 24. The medical probe of any of the previous clauses in which a spine retention hub is coupled to the distal end of the tubular shaft to connect the spines to the retention hub.

Clause 25. The medical probe of any of the previous clauses in which a cylindrical projection is provided to locate the reference electrode on the projection.

Clause 26. The medical probe of any of the previous clauses in which the spine retention hub includes outlet ports to allow fluid delivered to the distal end tubular shaft to exit the outlet ports into a volume surrounded by the basket spines.

Clause 27. A method of constructing a medical probe, the method comprising: aligning a spine of an expandable basket assembly with an electrode having a lumen extending through the body of the electrode; inserting the spine into the lumen of the electrode; and retaining the electrode on the spine with at least one biasing member.

Clause 28. The method of clause 27, in which the at least one biasing member is disposed outside of the lumen of the electrode.

Clause 29. The method of clause 27, in which the at least one biasing member is disposed inside the lumen of the electrode.

Clause 30. The method according to clause 27, further comprising: positioning the spine of the expandable basket assembly through a lumen of an electrically insulative jacket; positioning a wire through the lumen of the electrically insulative jacket; positioning the electrode over the electrically insulative jacket; and electrically connecting the wire to the electrode through an aperture in the electrically insulative jacket.

Clause 31. The method according to clause 31, wherein each respective spine of a plurality of spines comprises a first electrode and a second electrode, the method further comprising: aligning each respective spine of the plurality of spines with the first electrode and the second electrode; inserting each respective spine of the plurality of spines into a lumen of the first electrode and a lumen of the second electrode; and fitting an end of each respective spine of the plurality of spines to the tubular shaft sized to traverse vasculature.

Clause 32. The method according to any one of clauses 27-31, further comprising offsetting the electrodes between adjacent spines along the longitudinal axis.

Clause 33. The method according to any of clauses 27-31, wherein the electrode body lumen is configured to receive the wire of the medical probe.

Clause 34. The method according to any of clauses 26-32, wherein the wire is insulated from the spine.

What is claimed is:

1. A medical probe, comprising:

a tubular shaft including a proximal end and a distal end, the tubular shaft extending along a longitudinal axis of the medical probe; and an expandable basket assembly coupled to the distal end of the tubular shaft, the basket assembly comprising:

a plurality of spines extending along the longitudinal axis from a proximal central spine portion to a distal spine portion, the distal spine portion defining a cloverleaf structure disposed radially around the longitudinal axis, the cloverleaf structure defining a central cutout with a central area disposed about the longitudinal axis, the cloverleaf structure comprising:

a sinusoidal-like member extending from one spine to an adjacent spine in a direction around the longitudinal axis, the sinusoidal-like member meanders around:

(a) a first virtual circle having a first open area of approximately 20% that of the central area, the first virtual circle having its center located at a first distance to the longitudinal axis, (b) a second virtual circle having a second open area of approximately 90% of the first open area, the second virtual circle having its center located at a second distance smaller than the first distance to the longitudinal axis, and (c) a third virtual circle having its third open area approximately equal to the first open area, the third virtual circle having its center located at a third distance approximately equal to the first distance to the longitudinal axis.

2. The medical probe according to claim 1, wherein each spine of the plurality of spines includes at least one retention member extending generally transverse to the spine.

3. The medical probe of claim 2, in which the at least one retention member comprises a bow shaped member.

4. The medical probe of claim 2, in which the at least one retention member comprises two bow shaped members disposed in opposite direction and transverse to a longer length of each spine.

5. The medical probe of claim 2, further comprising:

a plurality of electrodes, wherein each electrode of the plurality of electrodes comprises a body defining a hollow portion extending through the body of the electrode so that a spine can be inserted into the hollow portion and retained by the at least one retention member.

6. The medical probe according to claim 5, wherein a cross-sectional shape of each electrode comprises a substantially ovoid or trapezoidal shape.

7. The medical probe of claim 5, in which the at least one retention member comprises first and second sets of retention members spaced apart along the spines, the first set includes two bow shaped members disposed in opposite direction and transverse to a longer length of each spine and the second set includes two bow shaped members disposed in opposite direction and transverse to a longer length of each spine so that each electrode is captured between the first and second sets of retention members.

8. The medical probe according to claim 1, wherein the central area comprises approximately 0.8 mm-squared area, a fourth virtual circle encircling the sinusoidal-like member comprises an area approximately 14 times greater than the central area and each of the first and third virtual circle is located at a first distance from the longitudinal axis while the second virtual circle is located at a second distance of approximately ½ that of the first distance.

9. The medical probe according to claim 8, in which the sinusoidal-like member is tangential to a central circle of the central area.

10. The medical probe according to claim 1, further comprising a plurality of electrically insulative jackets each disposed between a respective spine of the plurality of spines and a respective electrode of a plurality of electrodes, thereby electrically isolating the respective electrode from the respective spine.

11. The medical probe according to claim 10, further comprising a wire disposed inside a respective jacket of the plurality of electrically insulative jackets, wherein the wire is electrically connected to the respective electrode.

12. The medical probe according to claim 1, wherein the plurality of spines extends from the proximal central spine portion in an equiangular pattern such that respective angles between respectively adjacent spines are approximately equal.

13. The medical probe according to claim 1, wherein each respective spine of the plurality of spines comprises two electrodes.

14. The medical probe according to claim 1, further comprising:

a plurality of electrodes configured to deliver electrical pulses for irreversible electroporation, the pulses including a peak voltage of at least 900 volts (V).

15. The medical probe according to claim 1, wherein the plurality of spines is configured to form an approximately spherically-shaped basket assembly when in an expanded form.

16. The medical probe according to claim 1, wherein the plurality of spines is configured form an approximately oblate-spheroid basket assembly when in an expanded form.

17. The medical probe according to claim 1, in which the central cutout approximates a central circle with a central area and wherein the cloverleaf structure is disposed within a fourth circle with its center on the longitudinal axis so that portions of the cloverleaf close to the center circle is spaced apart along the longitudinal axis with respect to portions of the cloverleaf close to the fourth circle thereby defining a concave cloverleaf structure.

18. The medical probe according to claim 1, in which the cloverleaf structure is concave with its center extending towards the proximal central spine portion of the basket to approximate a concave surface disposed about the longitudinal axis.

19. The medical probe according to claim 1, in which a reference electrode is disposed proximate the distal end of the tubular shaft.

20. The medical probe according to claim 1, in which a spine retention hub is coupled to the distal end of the tubular shaft to connect the spines to the retention hub.

* * * * *